US007256392B2

(12) United States Patent
Sendai et al.

(10) Patent No.: US 7,256,392 B2
(45) Date of Patent: Aug. 14, 2007

(54) INSPECTION METHOD OF RADIATION IMAGING SYSTEM AND MEDICAL IMAGE PROCESSING APPARATUS USING THE SAME, AND PHANTOM FOR USE OF INSPECTION OF RADIATION IMAGING SYSTEM

(75) Inventors: Tomonari Sendai, Kaisei-machi (JP); Satoshi Arakawa, Kaisei-machi (JP); Masayuki Murakami, Old Greenwich, CT (US)

(73) Assignee: Fujifilm Corporation, Tokyo (JP)

( * ) Notice: Subject to any disclaimer, the term of this patent is extended or adjusted under 35 U.S.C. 154(b) by 211 days.

(21) Appl. No.: 10/790,142

(22) Filed: Mar. 2, 2004

(65) Prior Publication Data

US 2004/0227069 A1    Nov. 18, 2004

(30) Foreign Application Priority Data

Mar. 3, 2003   (JP)   ............................. 2003-055556
Mar. 10, 2003  (JP)   ............................. 2003-063428
Mar. 20, 2003  (JP)   ............................. 2003-076831

(51) Int. Cl.
*G01D 18/00*  (2006.01)
*G12B 13/00*  (2006.01)

(52) U.S. Cl. .................................. 250/252.1; 378/207
(58) Field of Classification Search ............. 250/252.1; 378/207
See application file for complete search history.

(56) References Cited

U.S. PATENT DOCUMENTS

| 4,126,789 | A  | * | 11/1978 | Vogl et al. .................. 378/145 |
| 5,539,799 | A  | * | 7/1996  | Schulze-Ganzlin et al. . 378/207 |
| 5,804,819 | A  | * | 9/1998  | Vuylsteke et al. ....... 250/252.1 |
| 6,231,231 | B1 | * | 5/2001  | Farrokhnia et al. ......... 378/207 |
| 6,694,047 | B1 | * | 2/2004  | Farrokhnia et al. ......... 382/132 |
| 2002/0067798 | A1 | * | 6/2002 | Lang ........................... 378/54 |

FOREIGN PATENT DOCUMENTS

| JP | 11-4822 A      | 1/1999  |
| JP | 2000-275758 A  | 10/2000 |
| JP | 2002-277992 A  | 9/2002  |
| JP | 2002-277993 A  | 9/2002  |
| JP | 2002-277995 A  | 9/2002  |
| JP | 2002-278004 A  | 9/2002  |

* cited by examiner

*Primary Examiner*—David Porta
*Assistant Examiner*—Shun Lee
(74) *Attorney, Agent, or Firm*—Sughrue Mion, PLLC

(57) ABSTRACT

A phantom, adapted to be radiation-imaged to obtain a radiation image for evaluation in inspection of a radiation imaging system, is capable of performing both the quantitative evaluation and the visual evaluation of the radiation image easily with a low cost and increasing accuracy of the constancy evaluation of the radiation imaging system. The phantom includes a base plate; a first member disposed on the base plate and having a first image quality evaluating pattern formed thereon to be used for visual evaluation as to a predetermined image quality evaluation item; and a second member disposed on the base plate and having a second image quality evaluating pattern formed thereon to be used for quantitative evaluation as to the predetermined image quality evaluation item.

10 Claims, 18 Drawing Sheets

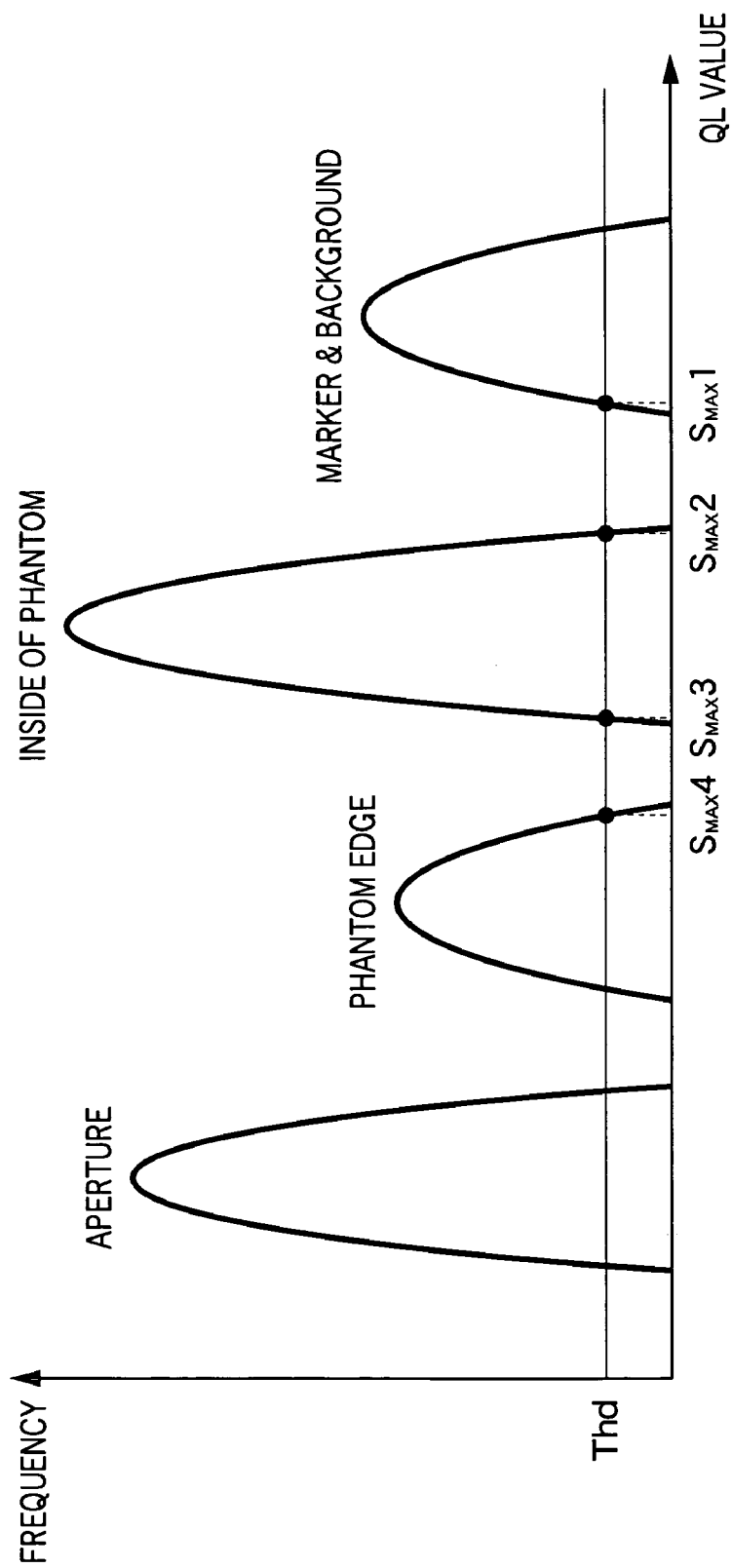

INSPECTION METHOD OF RADIATION IMAGING SYSTEM AND MEDICAL IMAGE PROCESSING APPARATUS USING THE SAME, AND PHANTOM FOR USE OF INSPECTION OF RADIATION IMAGING SYSTEM

BACKGROUND OF THE INVENTION

1. Field of the Invention

The present invention relates to an inspection method of radiation imaging system for inspecting quality of a radiation imaging system which includes an image reading apparatus for reading image information from a sheet recorded with a radiation image, and relates to a medical image processing apparatus using such inspection method. Further, the present invention relates to a phantom to be used for image quality control of a radiation image during the inspection of such radiation imaging system.

In this application, the word "radiation" is used in a wide sense so as to include a corpuscular beam such as an electron beam and an electromagnetic wave in addition to general radiation including X-ray, α-ray, β-ray, γ-ray, ultraviolet ray and so on.

2. Description of a Related Art

Conventionally, an imaging method using a radiation (X-ray, α-ray, β-ray, γ-ray, electron beam, ultraviolet ray and so on) is utilized in various fields, and particularly, employed as one of the most important means for diagnosis in a medical field. Since a first X-RAY photograph was realized, X-ray photography has been repeatedly improved and a method using a combination of a fluorescent screen and an X-ray film is predominantly used at present. On the other hand, in recent years, various digitized apparatuses such as X-ray CT apparatus, ultrasonic imaging apparatus, or MRI apparatus are practical use and construction of a diagnosis information processing system in hospitals is being developed. As for X-ray images, many studies have also been made for digitizing the systems, and a radiation imaging method using photostimulable phosphor has been established, whereupon there has been an increasing interest in such techniques available as methods that will replace conventional X-ray photography.

The photostimulable phosphor (storage phosphor) is a substance which accumulates a part of radiation energy when irradiated with a radiation; and after that, emits photostimulable luminescent light corresponding to the accumulated energy when irradiated with an excitation light such as visible light. The presence of that has been long known. The radiation imaging method using the photostimulable phosphor will be described below. First, using an imaging apparatus, a radiation image of an object such as human body is taken on a sheet, to which photostimulable phosphor is applied, and recorded thereon. Then, using an image reading apparatus, the photostimulable phosphor sheet is scanned with excitation light such as a laser beam, and thereby photostimulable luminescent lighe is read out photoelectrically by a photo-multiplier of the image reading apparatus. Based on the analog image signals obtained as described above, digital image data is obtained. Further, after being appropriately processed by using a medical image processing apparatus, the image data is outputted to a display such as a CRT, or printed out on a film with a laser printer or the like. Consequently, a radiation image, in which the energy level of the radiation transmitted through the object is visualized by means of gray levels or gradation, is obtained.

When such radiation image is utilized for medical diagnosis, high reliability in the radiation imaging system has to be highly ensured. Therefore, the performance of the radiation imaging system has to be measured and verified as needed. The reason for this is that, when any portion of radiation imaging system including photostimulable phosphor sheet and image reading apparatus is degraded or any abnormality occurs thereon, no normal radiation image can be obtained, and the reliability in image analysis is reduced. Further, since the irradiation of high-level radiation energy adversely affects human body, the verification of the performance of the radiation imaging system is also important in view of safety.

Japanese Unexamined Patent Application Publication JP-2000-275758A (pp. 6-8, FIG. 1) discloses a radiation image reading apparatus in which the photoelectric reading means is prevented from being adversely affected even when the open/close member of the housing is opened, maintenance person is prevented from being accidentally exposed to the excitation light exceeding a prescribed level, and further, tests such as verification of sheet conveyance situation and so on can be carried out in the situation where the open/close member is opened.

In the above-mentioned radiation image reading apparatus disclosed in JP-2000-275758A, test image signals are previously prepared, and based on the test image signals, image data is generated. However, in this radiation image reading apparatus, no test can be carried out in the processes from the generation of the photostimulable luminescent light to the generation of the image data based on the image signal which is represented by means of photostimulable luminescent light.

Also, in the following patent documents, inspection methods of easily detecting abnormality of a radiation image filming apparatus are disclosed. In the inspection method disclosed in Japanese Unexamined Patent Application Publication JP-2002-277992A (pp. 4-5, FIG. 3), ultraviolet ray is uniformly irradiated over the entire surface of a photostimulable phosphor detector (sheet), and photostimulable phosphor, which is generated by irradiating an excitation light on the photostimulable phosphor detector, is photoelectrically amplified. However, according to this inspection method, only limited items such as S-value representing the density of output image, uniformity of the density, granularity and the like can be inspected.

Japanese Unexamined Patent Application Publication JP-2002-277993A (PP. 3-4, FIG. 3) discloses an inspection method in which no additional imaging for the purpose of inspection is needed because image data obtained by imaging an object is used for the inspection. Further, Japanese Unexamined Patent Application Publication 2002-277995 (pp. 3-4, FIG. 4) discloses an inspection method in which excitation light, which is modulated such that the space of non-radiated area changes wider and narrower, is irradiated on a photostimulable phosphor detector (sheet), and then, difference between the read out signal (image signal) from the photostimulable phosphor detector and the modulation state of the excitation light is numerically calculated. However, according to these inspection methods, only limited items such as S-value, resolution and the like can be inspected.

In an inspection method disclosed in Japanese Unexamined Patent Application Publication JP-2002-278004A (pp. 4-5, FIG. 3), test light of blue light irradiated from a light source disposed in a position adjacent to a photostimulable phosphor detector (sheet) is guided to a photo-multiplier by using a light collection unit and amplified photoelectrically by using a photo-multiplier. However, according to this inspection method, only limited items such as light collection unit and the like can be inspected.

Accordingly, a method is desired which is capable of effectively inspecting radiation imaging system including radiation image reading apparatus.

Meanwhile, when inspecting a radiation imaging system, a physical phantom or a body imitation phantom is used. For example, in Japanese Unexamined Patent Application Publication JP-A-11-4822, there are disclosed image quality test phantom and method of automatic monitoring and evaluation of image quality in a digital X-ray visualization and imaging system. The physical phantom, which is also referred to as QC (quality control) phantom, is a phantom in which various members made by using materials such as metal and resin of which radiation absorption coefficients are known, are disposed on a base plate. Each of the members has a predetermined size, shape, density, composition and so on, and they are used as image quality evaluating patterns. Those image quality-evaluating patterns are designed so as to enable measurement of one or plural image quality evaluation items pertaining to a radiation imaging system.

The radiation imaging is performed by irradiating a radiation such as X-ray on a QC phantom as described above, and the radiation image information of the QC phantom is recorded on a recording medium such as the photostimulable phosphor sheet. The recording medium is subjected to a predetermined processing to generate a radiation image, which is displayed on a CRT monitor or the like. This radiation image is analyzed as to predetermined image evaluation items so that the constancy or invariance of various performance parameters of the radiation imaging system are evaluated thereby the quality inspection of the radiation imaging system is carried out.

The evaluation of the constancy or invariance of the performance parameters is made in a manner of quantitative evaluation and visual evaluation. The quantitative evaluation means an inspection in which the evaluation is made quantitatively by processing including calculation processing of digital data. On the other hand, the visual evaluation means an inspection to be performed in a manner other than the above quantitative evaluation, for example, an inspection in which an operator evaluates a radiation image in a manner of visual observation. In these inspections, the visual evaluation can be easily carried out relatively. However, since the visual evaluation depends on the operator's subjective feeling, no objectivity can be expected. On the other hand, the quantitative evaluation can provide objective evaluation but requires a lot of labor for the operation. Generally, the visual evaluation is carried out more frequently than the quantitative evaluation. For example, the visual evaluation is carried out every week, while the quantitative evaluation is carried out once per three months. Further, in the case where the constancy evaluation is made in large-scale facilities, ten or more reading apparatus are usually provided. In view of such circumstances, there is a need for an efficient workability.

However, an ordinary QC phantom is not designed to enable both of the visual evaluation and the quantitative evaluation for one image quality evaluation item. For example, in the case where objective measurement results of image quality parameters are required after a visual evaluation, it is therefore required to mount a new phantom specialized or dedicated for quantitative evaluation and resume the measurement starting from the radiation imaging. That is, it is necessary to change one to another of dedicated phantoms depending on which of the visual evaluation and the quantitative evaluation is made. Accordingly, the verification operation of the radiation imaging system becomes complicated, and therefore, a lot of labor as well as time consumption are required.

Further, when the visual evaluation and the quantitative evaluation are carried out by using different phantoms, there arises a difficulty to compare the measurement results thereof and consider the measurement results. Accordingly, result of the visual evaluation cannot be evaluated from further objective viewpoint. Therefore, no precise constancy evaluation can be obtained, and there arises such problem that no reliability in the evaluation can be ensured. Furthermore, since two phantoms for visual evaluation and quantitative evaluation are required, there occurs another problem that the cost thereof increases, that is, uneconomical.

Still further, in order to ensure the reliability in the inspection accuracy, it is required that an image of QC phantom is displayed at a proper reference region in the radiation image by mounting the QC phantom in a proper position corresponding to a reference position or an inspection object area within the recording medium at the time of imaging. Therefore, in the case where the QC phantom is mounted out of the proper position, the image of the QC phantom is not display ed in the proper reference region in the radiation image, and the imaging has to be carried out again after correcting the position of the QC phantom. This may lead to the interruption as well as the complication of the inspection operation. Thus, there arises still another problem that automation of the inspection operation is largely prevented.

SUMMARY OF THE INVENTION

The present invention has been made in view of the above-mentioned circumstances. A first object of the present invention is to carry out both the quantitative evaluation and the visual evaluation of a radiation image easily with a low cost and to increase accuracy in the constancy evaluation of the radiation imaging system. Also, a second object of the present invention is, when carrying out the inspection of a radiation imaging system, to enable closer inspection as far as detailed items by using a radiation image obtained by a single imaging. Further, a third object of the present invention is, when carrying out the inspection of the radiation imaging system, to ensure the reliability in the inspection accuracy without being adversely influenced by the mounting position of the phantom and to promote further automation of the inspection operation.

In order to solve the above-mentioned problems, according to a first aspect of the present invention, there is provided a phantom for use in inspection of radiation imaging system which inspection is carried out by evaluating a radiation image obtained by imaging the phantom by using the radiation imaging system as to at least one image quality evaluation item, wherein the phantom comprises: a base plate; a first member disposed on the base plate and having a first image quality evaluating pattern formed thereon to be used for visual evaluation as to a predetermined image quality evaluation item; and a second member disposed on the base plate and having a second image quality evaluating pattern formed thereon to be used for quantitative evaluation as to said predetermined image quality evaluation item.

According to a second aspect of the present invention, there is provided a phantom for use in inspection of radiation imaging system which inspection is carried out by evaluating a radiation image obtained by imaging the phantom by using the radiation imaging system as to at least one image quality evaluation item, wherein the phantom comprises: a base plate; at least one member disposed on the base plate and having an image quality evaluating pattern formed thereon to be used for a predetermined image quality evaluation item; and a plurality of markers, respectively disposed at a plurality of positions different from each other on the base plate, for use of detecting a position of the image quality evaluating pattern in the radiation image.

According to a first aspect of the present invention, there is provided a medical image processing apparatus for evaluating image quality of a radiation image obtained by using a radiation imaging system which performs radiation imaging to record radiation image information on a recording medium, reads out the radiation image information from the recording medium to generate image data, and performs a predetermined image processing for the image data to display or output a radiation image, thereby inspecting the radiation imaging system, wherein the apparatus comprises: image processing means for performing image processing on input image data; measuring means for performing, when image data representing a radiation image obtained by imaging a phantom having a plurality of image quality evaluating patterns as to a predetermined image quality evaluation item is inputted, measurement with respect to the input image data as to said predetermined image quality evaluation item; inputting means to be used for inputting inspection result as to the predetermined image quality evaluation item obtained by visually observing the displayed or outputted radiation image; and determination means for determining the image quality of the radiation image on the basis of measurement result obtained by the measuring means and the inspection result inputted by using the inputting means.

According to a second aspect of the present invention, there is provided a medical image processing apparatus for evaluating image quality of a radiation image obtained by using a radiation imaging system, thereby performing inspection of the radiation imaging system, wherein the apparatus comprises: position detecting means for detecting, when image data representing a radiation image obtained by imaging a phantom having an image quality evaluating pattern as to at least one image quality evaluation item and a plurality of markers respectively disposed at a plurality of positions different from each other by using the radiation imaging system is inputted, a position of the phantom in the radiation image by using the plurality of markers; comparison and calculating means for comparing the position of the phantom detected by the position detecting means with a reference position of the phantom in the radiation image and calculating an amount of difference in a linear direction and a rotational direction; search area changing means for changing a search area, which is a region within the radiation image to be measured as to a predetermined image quality evaluation item, on the basis of the amount of difference calculated by the comparison and calculating means; physical amount calculating means for performing measurement as to the predetermined image quality evaluation item within the search area changed by the search area changing means and calculating a physical amount representing characteristic of the radiation image; determination criterion changing means for changing a determination criterion to be used for determining the image quality of the radiation image, on the basis of the amount of difference calculated by the comparison and calculating means; and determination means for determining the image quality of the radiation image using the physical amount calculated by the physical amount calculating means, on the basis of the determination criterion changed by the determination criterion changing means.

According to a third aspect of the present invention, there is provided a medical image processing apparatus for evaluating image quality of a radiation image obtained by using a radiation imaging system, thereby performing inspection of the radiation imaging system, wherein the apparatus comprises: position detecting means for detecting, when image data representing a radiation image obtained by imaging a phantom having an image quality evaluating pattern as to at least one image quality evaluation item and a plurality of markers respectively disposed at a plurality of positions different from each other by using the radiation imaging system is inputted, a position of the phantom in the radiation image by using the plurality of markers; comparison and calculating means for comparing the position of the phantom detected by the position detecting means with a reference position of the phantom in the radiation image, and calculating an amount of difference in a linear direction and a rotational direction; image correcting means for correcting the position of the phantom in the radiation image so that the amount of difference calculated by the comparison and calculating means is reduced; physical amount calculating means for performing measurement with respect to an image of the phantom, of which position is correct by the image correcting means, as to a predetermined image quality evaluation item, and calculating a physical amount representing the characteristic of the radiation image; and determination means for determination the image quality of the radiation image on the basis of the physical amount calculated by the physical amount calculating means.

According to a first aspect of the present invention, there is provided a method of evaluating image quality of a radiation image obtained by using a radiation imaging system, thereby inspecting the radiation imaging system, wherein the method comprises the steps of: (a) inputting image data representing a radiation image obtained by radiation imaging of a phantom having a plurality of image quality evaluating patterns as to image quality evaluation items including at least measurement of linearity, sharpness and contraction ratio; (b) detecting a position of the phantom in the radiation image on the basis of the image data inputted at step (a); (c) performing measurement as to the image quality evaluation items including measurement of at least linearity, sharpness and contraction ratio on the image of the phantom on the basis of the image data inputted at step (a); and (d) determining the image quality of the radiation image on the basis of measurement result measured at step (c).

According to a second aspect of the present invention, there is provided a method of evaluating image quality of a radiation image obtained by using a radiation imaging system for performing radiation imaging to record radiation image information on a recording medium, reading out the radiation image information from the recording medium to generate image data, subjecting the image data to a predetermined image processing to display or output the radiation image, thereby inspecting the radiation imaging system, wherein the method comprises the steps of: (a) inputting an image data representing a radiation image obtained by radiation imaging of a phantom having an image quality evaluating pattern to be used for visual evaluation and an image quality evaluating pattern to be used for quantitative evaluation as to a predetermined image quality evaluation item; (b) performing quantitative measurement with respect to the image data inputted at step (a) as to the predetermined image quality evaluation item; (c) displaying or outputting the radiation image on the basis of the image data inputted at step (a) and visually observing the displayed or outputted radiation image to perform inspection as to the predetermined image quality evaluation item; and (d) determining the image quality of the radiation image on the basis of measurement result obtained at step (b) and inspection result obtained at step (c).

According to a third aspect of the present invention, there is provided a method of evaluating image quality of a radiation image obtained by using a radiation imaging system, thereby inspecting the radiation imaging system, wherein the method comprises the steps of: (a) inputting an image data representing a radiation image obtained by radiation imaging of a phantom having an image quality evaluating pattern as to at least one image quality evaluation item and a plurality of markers respectively disposed at a plurality of positions different from each other; (b) detecting a position of the phantom in the radiation image by using the plurality of markers on the basis of the image data inputted at step (a); (c) comparing the position of the phantom detected at step (b) with a reference position of the phantom in the radiation image, and calculating an amount of difference in a linear direction and a rotational direction; (d) changing a search area, which is a region within the radiation image to be measured as to a predetermined image quality evaluation item, on the basis of the amount of difference calculated at step (c); (e) performing measurement in the search area changed at step (d) as to the image quality evaluation items, and calculating a physical amount representing characteristic of the radiation image; (f) changing a determination criterion to be used for evaluating the image quality of the radiation image on the basis of the amount of difference calculated at step (c); and (g) evaluating the image quality of the radiation image by using the physical amount calculated at step (e) on the basis of the determination criterion changed at step (f).

According to a fourth aspect of the present invention, there is provided a method of evaluating image quality of a radiation image obtained by using a radiation imaging system, thereby inspecting the radiation imaging system, wherein the method comprises the steps of: (a) inputting an image data representing a radiation image obtained by radiation imaging of a phantom having an image quality evaluating pattern as to at least one image quality evaluation item and a plurality of markers respectively disposed at a plurality of positions different from each other; (b) detecting a position of the phantom in the radiation image by using the plurality of markers on the basis of the image data inputted at step (a); (c) comparing the position of the phantom detected at step (b) with a reference position of the image of the phantom in the radiation image, and calculating an amount of difference in a linear direction and a rotational direction; (d) correcting the position of the phantom in the radiation image so that the amount of difference calculated at step (c) is reduced; (e) performing measurement with respect to the image of the phantom, of which position has been corrected at step (d), as to a predetermined image quality evaluation item, and calculating a physical amount representing characteristic of the radiation image; and (f) determining the image quality of the radiation image on the basis of the physical amount calculated at step (e).

BRIEF DESCRIPTION OF THE DRAWINGS

FIG. 8 is a flowchart (first half) showing the process of detecting a marker image and calculating position difference due to parallel and rotational shifts and so on;

FIG. 9 is a flowchart (second half) showing the process of detecting a marker image and calculating position difference due to parallel and rotational shifts and so on;

FIG. 10 is a histogram showing density distribution of images within a search region.

DESCRIPTION OF THE PREFERRED EMBODIMENTS

Figure 1:
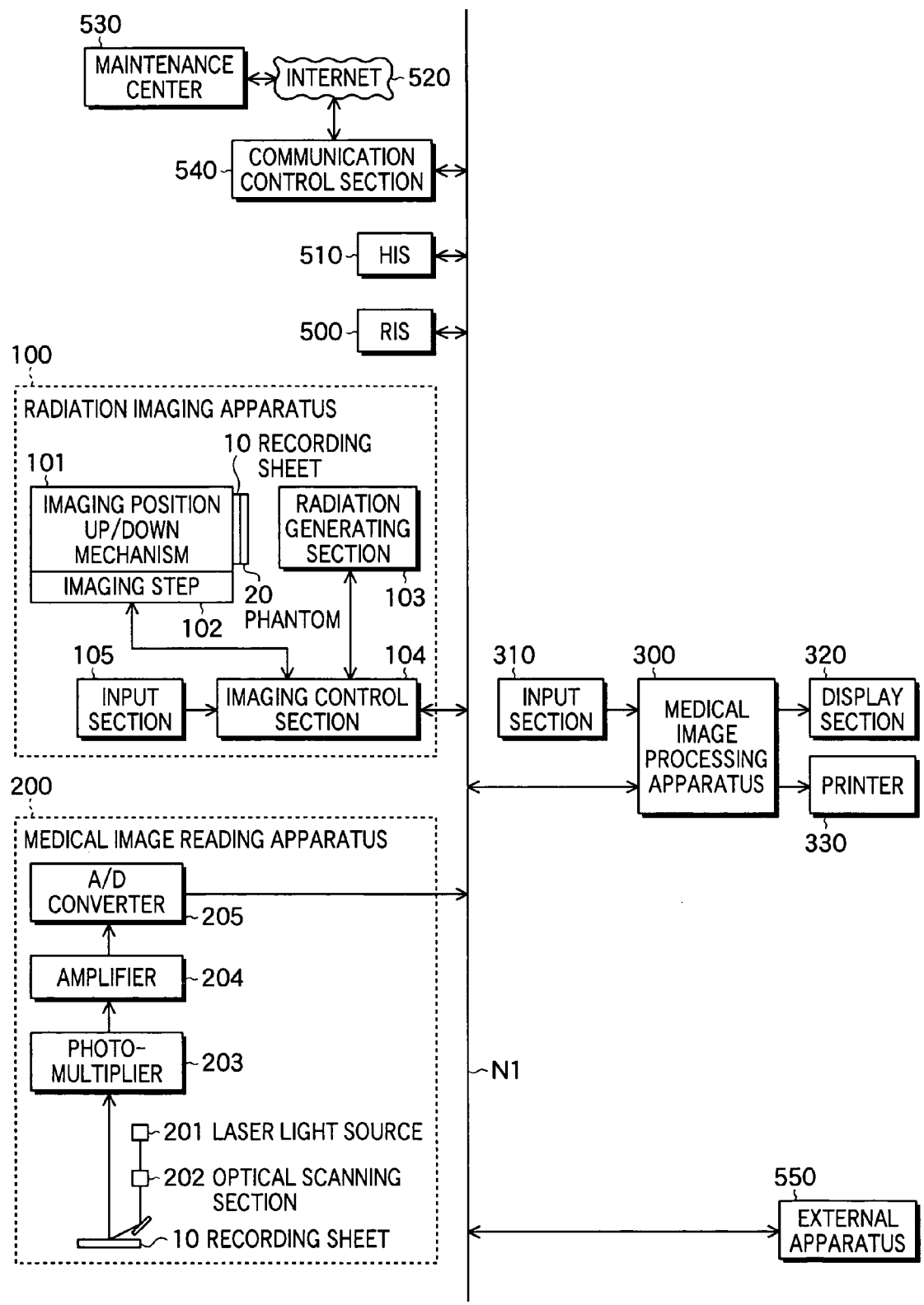
FIG. 1 is a block diagram showing a construction of a radiation imaging system which includes a medical image processing apparatus according to a first embodiment of the present invention.

Embodiments of the present invention will be described below by referring to the drawings. The same constituent elements will be given with the same reference numerals and the descriptions thereof will be omitted. In this application, the words "quantitative evaluation" mean an inspection in which processing including calculation processing is made in terms of digital data, which represents a radiation image of an image quality controlling phantom (a structure for inspection) or the like obtained by radiation imaging, and thereby quantitative measurement is made based on the measurement results so as to obtain inspection quantitative values, determination of conformity/non-conformity in the inspection, and soon. Further, in this application, the words "visual evaluation" mean an inspection which is made by means of an inspection other than the above-described quantitative evaluation in terms of a radiation image of the above-mentioned phantom or the like, particularly, an inspection which is made by an operator by observing a radiation image as shown on a display or a film.

FIG. 1 is a block diagram showing a construction of a radiation imaging system which includes a medical image processing apparatus according to a first embodiment of the present invention.

As shown in FIG. 1, the radiation imaging system includes a radiation imaging apparatus 100 that performs radiation imaging to record radiation image information on a recording sheet 10, a medical image reading apparatus 200 that reads radiation image information recorded in the recording sheet 10 to generate image data, and a medical image processing apparatus 300 that performs predetermined processing in terms of the image data inputted from the medical image reading apparatus 200. These radiation imaging apparatus 100, medical image reading apparatus 200, and medical image processing apparatus 300 are connected to each other via a network N1.

Connected to the network N1 are a radiology information system (RIS) 500 which is used for controlling various operations in terms of radiation imaging, a hospital information system. (HIS) 510 which is used for controlling the entire hospital, and a communication control section 540 for communicating with a maintenance center 530 through the Internet 520. Further, depending on the necessity, external apparatus 550 such as a database server of the hospital, ID card readers and terminal devices are connected to the network N1.

The radiation imaging apparatus 100 is an apparatus that irradiates with the radiation the recording sheet 10 through an object, and thereby records the radiation transmitted through the object on the recording sheet 10 as radiation image information about the object. The recording sheet 10 is a sheet (photostimulable phosphor sheet) applied with a photostimulable phosphor material, which accumulates the energy of the radiation, and is used as the recording medium for recording the radiation image information.

The radiation imaging apparatus 100 includes a imaging position up/down mechanism 101 that moves the position of the recording sheet 10 up/down to adjust the imaging position of the object, an imaging step 102 for positioning the feet of the object, a radiation generating section 103 for generating radiation to irradiate the object, an imaging control section 104 that controls the radiation generating section 103 and so on in accordance with given imaging conditions, an input section 105 that is used for inputting various instructions and imaging conditions. The imaging control section 104 is connected to the network N1; thus imaging conditions can be set up through the network N1.

When the inspection of the radiation imaging system is carried out, the phantom 20 is disposed in the radiation imaging apparatus 100 as the object. By carrying out the radiation imaging under the predetermined imaging conditions, the radiation image information of the phantom 20 is recorded on the recording sheet 10. After imaging, the recording sheet 10 is set to a predetermined position of the medical image reading apparatus 200. As, for the phantom 20, detailed description will be made later.

The medical image reading apparatus 200 photoelectrically reads radiation image information recorded on the recording sheet 10, and converts the energy level of the radiation irradiated on the recording sheet 10 into data, thereby generates image data. The reading of the radiation image information is carried out as described below. That is, the surface of the recording sheet 10 is scanned by means of light beam, which has been emitted from a laser light source 201 and passed through an optical scanning section 202. As a consequence, from the region of the recording sheet 10 irradiated with the light beam, photo stimulable luminescent light of an amount corresponding to the accumulated radiation energy is generated. The photostimulable luminescent light is guided by an optical guide and photoelectrically detected by a photo-multiplier 203 and outputted as an analog signal representing the radiation image information. Further, this analog signal is amplified by an amplifier 204, and digitized by an A/D converter 205. The image data, which has been generated as describe above, is outputted to the medical image processing apparatus 300 along with information incidental to the image through the network N1.

Alternately, as the method in the medical image reading apparatus, another method as described below may be adopted. That is, as the light source for energizing the photostimulable luminescent light, a line light source in which LEDs or the like are disposed in the primary scanning direction is used, and as the detector for detecting the photostimulable luminescent light, a scanning head having a line sensor of CCDs or the like disposed in the primary scanning direction is used. While relatively moving the scanning head and the photostimulable phosphor sheet 10 in the secondary scanning direction perpendicular to the primary scanning direction, the excitation light emitted from the line light source is allowed to be made incident on the photostimulable phosphor sheet 10, and the photostimulable luminescent light generated from the photostimulable phosphor sheet 10 is read by the line sensor.

The medical image processing apparatus 300 performs image processing on the image data, which is generated in the medical image reading apparatus 200, to generate radiation image, and performs measurement on the radiation image as to predetermined image quality evaluation items so as to inspect the constancy, etc. on the performance and parameters of the radiation imaging system. The medical image processing apparatus 300 is constituted of, for example, a personal computer. The medical image processing apparatus 300 is provided with a input section 310 such as a keyboard and a mouse, which are used for inputting various instructions and inspection results or the like, a display section 320 such as a CRT monitor for displaying radiation images, and a printer 330 for printing medical diagnostic images on a film or the like.

Figure 2:
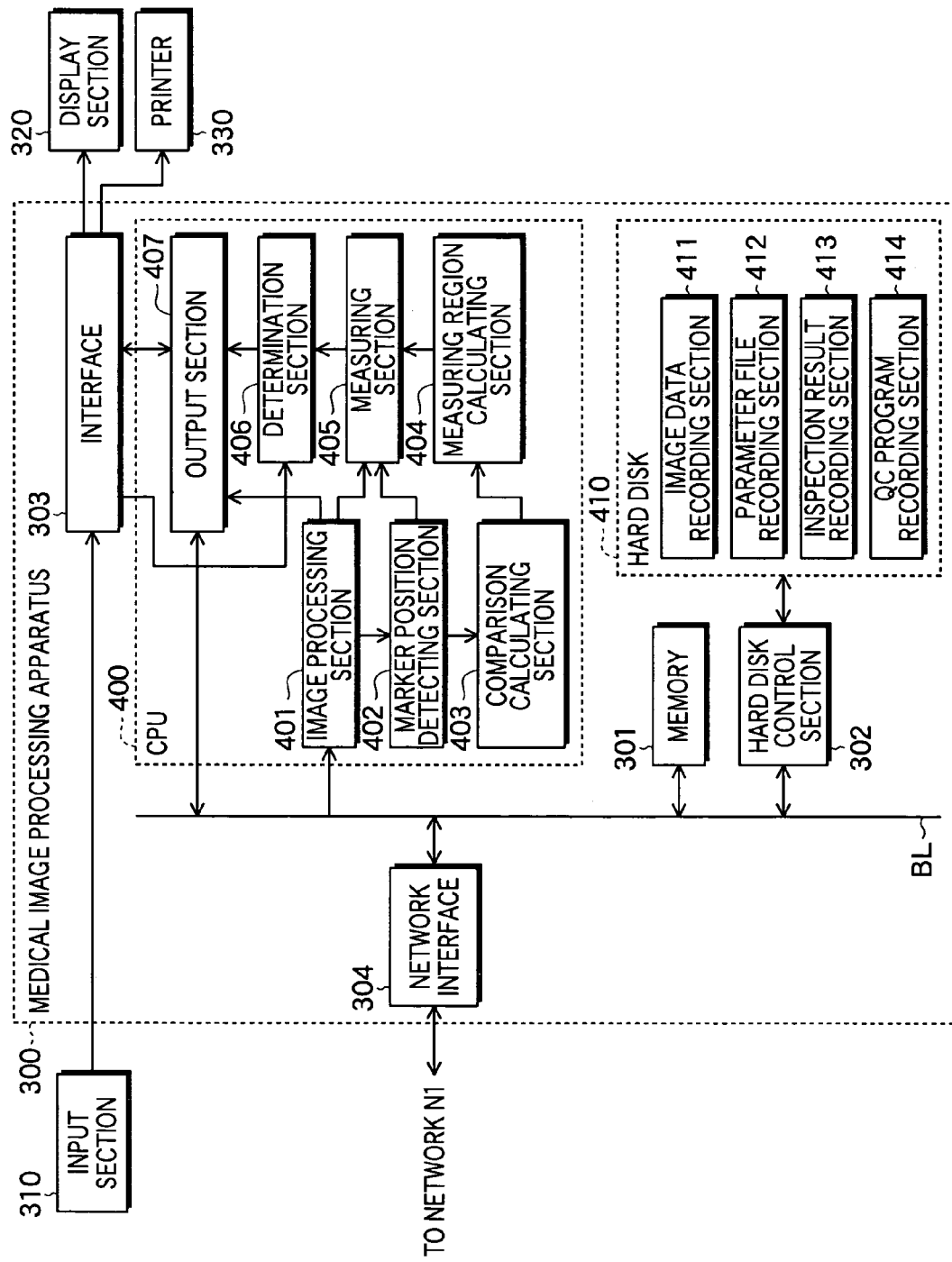
FIG. 2 is a block diagram showing the configuration of the medical image processing apparatus as shown in FIG. 1.

FIG. 2 is a block diagram showing the configuration of the medical image processing apparatus 300 shown in FIG. 1 in detail. The medical image processing apparatus 300 includes a memory 301 for temporary storing the input image data and information incidental to the image, a hard disk control section 302, an interface 303, a network interface 304, a central processing unit (hereinafter, referred to as CPU) 400, and a hard disk 410 as the recording medium. The memory 301, the hard disk control section 302, the network interface 304, and the CPU 400 are connected to each other through a bus line BL.

The CPU 400 is connected to the input section 310, the display section 320 and the printer 330 through the interface 303. Further, the CPU 400 is connected to the radiation imaging apparatus 100, the medical image reading apparatus 200, the RIS 500, the HIS 510 and the communication control section 540 as shown in FIG. 1 through the network interface 304 and the network N1.

In the hard disk 410, a basic program for operating the CPU 400, software including a program (QC program) to be used for performing the inspection of the radiation imaging system, and information to be used for processing the above are stored. In FIG. 2, an image data recording section 411 for recording the image data and the information incident to the image, a parameter file recording section 412 for recording the parameters to be used when the inspection is carried out, an inspection result recording section 413 for recording historical information of the inspection results of the radiation imaging system, and a QC program recording section 414 are shown. As for the recording medium, in addition to the internal hard disk 410, an external hard disk, a flexible disk, MO, MT, RAM, CD-ROM, DVD-ROM or the like may be used.

Next, the functional blocks 401-407 as shown in FIG. 2 will be described. These functions are for inspecting the quality of the radiation imaging system as shown in FIG. 1 by evaluating the image quality of the radiation image obtained by performing radiation imaging of a phantom, which will be described later. In this embodiment, these functional blocks 401-407 are realized by the CPU 400 and the software (program).

The image processing section 401 performs a predetermined image processing such as standardization, gradation processing, logic read processing on the image data inputted from the medical image reading apparatus 200.

Based on the image data which has been processed with image processing in the image processing section 401, the marker position detecting section 402 detects the position of images representing markers disposed on the phantom in the recording sheet 10.

The comparison calculating section 403 calculates the amount of position difference of the images representing the phantom 20 in the parallel direction and the rotational direction with respect to the recording sheet 10, based on the position of the detected marker image.

The measuring region calculating section 404 calculates the region on the radiation image, which region becomes the object to be measured when the inspection is carried out, based on the calculated amount of position difference.

The measuring section 405 performs the measurement on the image data, which has been subjected to the image processing, in terms of the image quality evaluation item to be quantitatively evaluated based on the calculated measuring region, and calculates physical amount necessary for evaluating of the image quality. As for the image quality evaluation item to be visually evaluated, an operator visually inspects the radiation image displayed on the display section 320. The inspection results by the operator are inputted to the medical image processing apparatus 300 by using the input section 310.

Based on the measurement results, which has been inputted from the measuring section 405, and the inspection results, which has been made by the operator and inputted through the input section 310, the determination section 406 determines whether any abnormality is found in terms of each image quality evaluation item, and creates determination results.

The output section 407 outputs image data which has been subjected to the image processing in the image processing section 401, the determination results which has been created by the determination section 406 and the like, to the display section 320 or the printer 330 through the interface 303. The inspection results and the determination results in terms of each image quality evaluation item are also accumulated in the hard disk 410.

Next, the phantom according to an embodiment of the present invention will be described with reference to FIG. 3 and FIGS. 4A-4E. The phantom according to this embodiment is a phantom for controlling the image quality, which phantom is used when inspecting the quality of the radiation imaging system as shown in FIG. 1. Hereinafter, the phantom for controlling the image quality such as used in this embodiment, will be referred to as QC (quality control) phantom.

Figure 3:
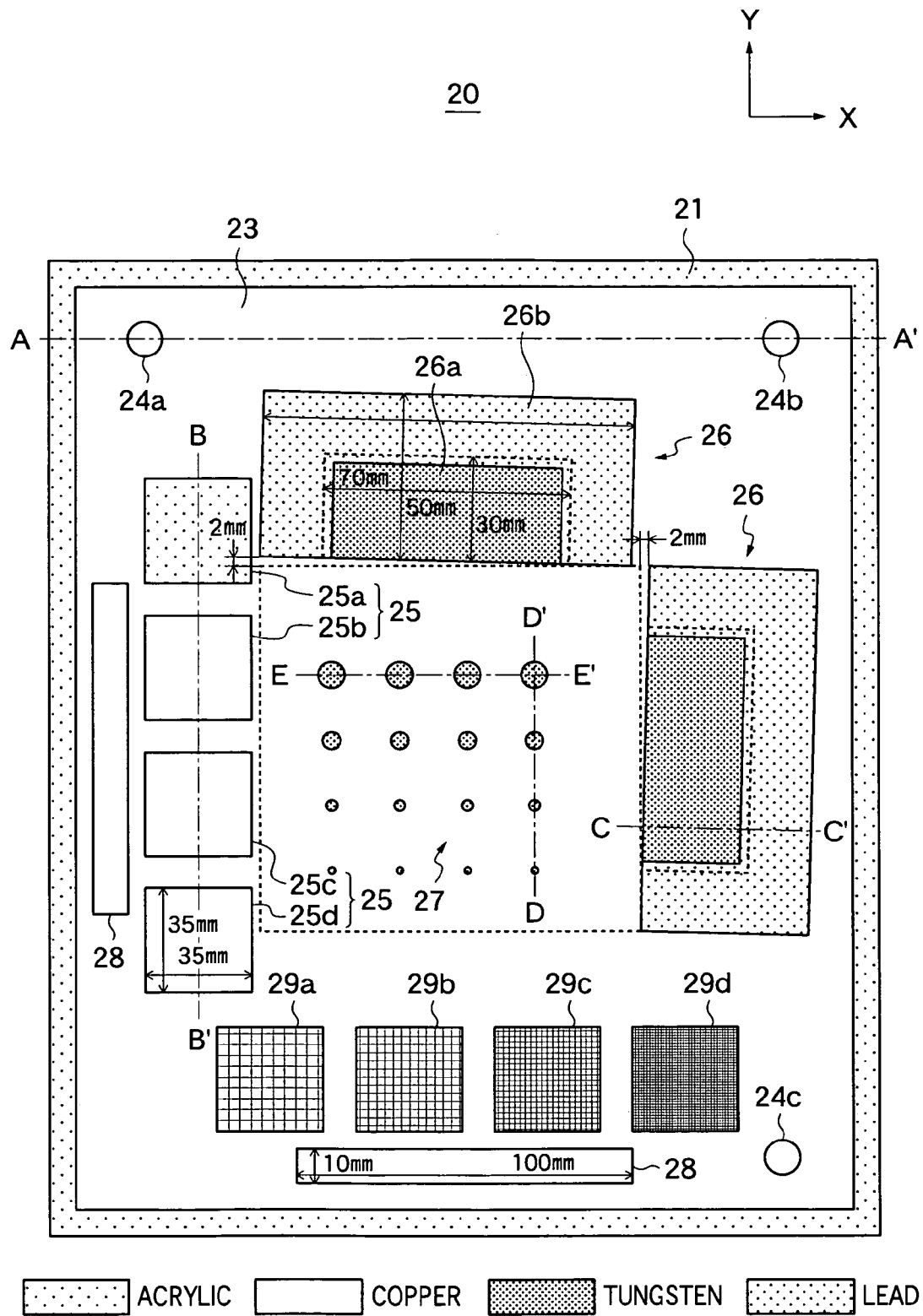
FIG. 3 is a plan view showing the constitution of a phantom according to an embodiment of the present invention.

FIG. 3 is a plan view showing the constitution of a QC phantom according to this embodiment. Also, FIGS. 4A-4E show the section of the QC phantom 20 taken along the lines A-A' to E-E' as shown in FIG. 3 respectively. As shown in FIG. 3, in the QC phantom 20, various image quality measuring patterns 25-29, which are formed from members such as acrylic, copper, tungsten, lead, mesh and so on, are disposed. These image quality-measuring patterns correspond to a plurality of image quality evaluation items which are used when evaluating the radiation image. In this embodiment, the image quality measuring patterns are disposed such that both the quantitative evaluation and the visual evaluation can be carried out as to at least one image quality evaluation item in those image quality evaluation items. Further, in this embodiment, in the measurable image quality evaluation items, linearity, dynamic range, sharpness (resolution), contrast, S/N ratio and contraction ratio of the image are included.

Figure 4A:
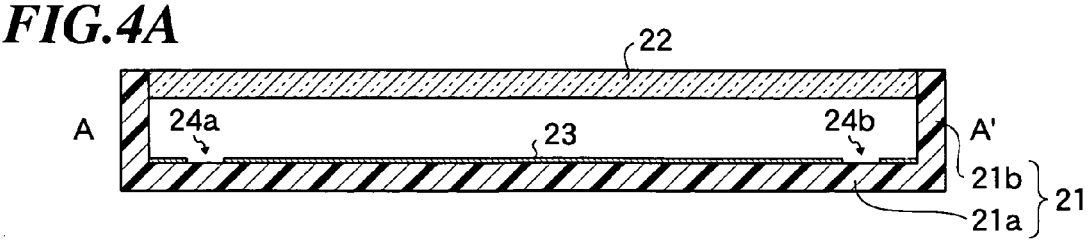
FIG. 4A-4E are views showing sections of a phantom taken along the lines A-A' to E-E' as shown in FIG. 3.

As shown in FIG. 4A, the QC phantom 20 is constituted by disposing various members in a space enclosed by a white acrylic case 21 and a white or transparent acrylic cover 22. In FIG. 3, in order to illustrate the inside of the QC phantom 20, the acrylic cover 22 is not shown in FIG. 4A.

The acrylic case 21 includes a base plate 21a on which various members are disposed and a side wall 21b enclosing the periphery of the base plate 21a. These base plate 21a and the side wall 21b may be integrally formed, or may be formed separately and bonded to each other. Also, on the bottom surface inside the acrylic case 21, a copper plate 23 is placed.

As shown in FIG. 3, in the QC phantom 20, three markers 24a-24c are disposed. The markers 24a-24c are used to obtain the geoemetrical position of the QC phantom images, which are recorded on the recording sheet 10, on the recording sheet 10 (hereinafter, referred to as phantom image), thereby, to detect the position of the images of the image quality measuring patterns 25-29 (hereinafter, referred to as pattern image). In order to readily and reliably detect the radiation images of the markers (marker images), it is preferred that the markers 24a-24c have a radiation transmittance different from that of the other portion of the QC phantom 20, and that the markers 24a-24c are formed in shapes different from those of the other image quality measuring patterns 25-29. As shown in FIG. 4A, in this embodiment, these markers 24a-24c are formed by cutting copper plate 23 in the areas of circles having a diameter of, for example, 5 mm.

By detecting the position of the pattern images by using the markers, the correctness of the quality inspection of the radiation imaging system can be increased, and the image processing and the processing of the image quality evaluation items can be readily automatized. The markers 24a-24c may be used for positional alignment of the QC phantom 20.

Figure 4B:
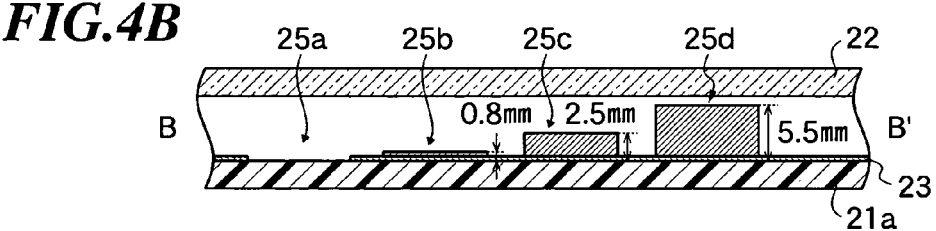

As shown in FIG. 3, disposed in the QC phantom 20 are copper step patterns 25 including a plurality of copper plates, which are disposed at step-like configuration and different from each other in thickness. The copper step patterns 25 are used for inspecting the linearity and dynamic range of the brightness of the image, which depend on the difference of the radiation dose obtained by irradiating the recording sheet, by means of visual evaluation by the operator or quantitative evaluation. The reason for this is as described below. That is, since the intensity of radiation transmitting the copper plate is inversely proportional to the thickness thereof, by using the copper plates having the thickness different from each other (including thickness of zero), the intensity level from the maximum intensity to the minimum intensity can be given. As shown in FIG. 4B, in this embodiment, the thicknesses of these patterns 25a-25b are set to be 0 mm, 0.8 mm, 2.5 mm and 5.5 mm including the thickness of the copper plate 23, respectively. The pattern 25a having a thickness of 0 mm is formed by cutting through the copper plate 23. The number, the size and the thickness of the copper plates included in the step pattern are not limited to this embodiment, but the step pattern may be constituted by using copper plates having various sizes and thicknesses.

Figure 4C:
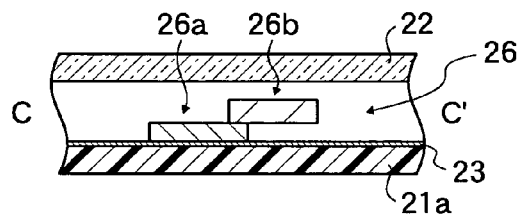

As shown in FIG. 3, disposed in the QC phantom 20 are two edges detecting patterns 26, which are formed with sharp edge portions. The edge detecting patterns 26 are used for quantitatively evaluating the sharpness of a radiation image. By differentiating the image of sharp-angled edge portions disposed on these edge-detecting patterns 26, line spread function is obtained, and then, by carrying out Fourier transformation, MTFs (modulation transfer functions) in the X-direction and the Y-direction are measured. In this embodiment, the two edge detecting patterns 26 are disposed being out of alignment by 5° respectively relative to the two edges of the QC phantom 20 which are perpendicular to each other (two scanning directions). Also, as shown in FIG. 4C, each of the edge detecting patterns 26 is disposed by using the tungsten plate 26a such that the lead member 26b is lifted up from the base plate 21a.

Figure 4D:
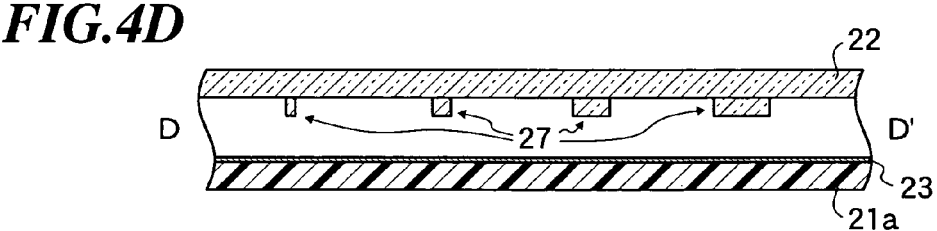
Figure 4E:
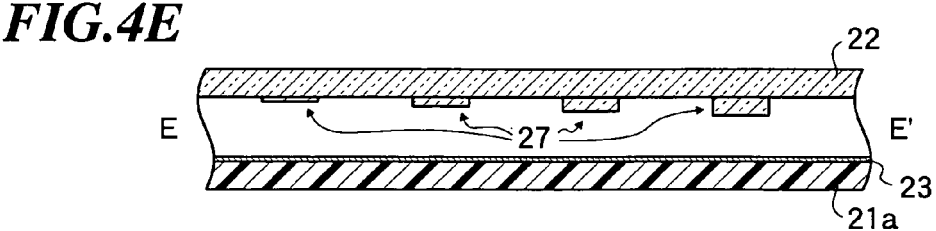

As shown in FIG. 3, disposed in QC phantom 20 is a Burgere's phantom (contrast resolution pattern) 27, which is formed of an acrylic member. The Burgere's phantom 27 is used for visual inspection of low contrast resolution, and thereby relative contrast and the S/N ratio of the radiation imaging system are verified. As shown in FIG. 3 or FIG. 4D, in this embodiment, in the direction of the line D-D', acrylic members having a predetermined thickness are disposed so that the diameters thereof change as 1 mm, 2 mm, 3 mm and 4 mm. On the other hand, as shown in FIG. 4E, in the direction of line E-E', acrylic members having a predetermined diameter are disposed so that the thickness thereof change as 1 mm, 1.5 mm, 2 mm and 3 mm.

As shown in FIG. 3, disposed in the QC phantom 20 are two copper scale patterns 28, which are formed of copper members. The copper scale patterns 28 are used for quantitative evaluation of the contraction ratio with respect to each scanning direction. In this embodiment, the size of these copper members is 100 mm in length, 10 mm in width, 0.5 mm in thickness, and these copper members are disposed such that the longitudinal edges of the copper members are parallel to the two edges of the QC phantom 20 which are perpendicular to each other (two scanning direction), respectively.

Further, disposed on the QC phantom 20 are wire mesh patterns 29. The wire mesh patterns 29 are used for visually evaluating the sharpness and nonuniformity of the radiation image. The wire meshes 29a-29d are preferably formed of steel meshes, and have a different wire pitch respectively. By comparing the non-uniformity of the sharpness between the wire meshes 29a-29d, the non-uniformity of the sharpness is widely evaluated based on the entire thereof. In this embodiment, the wire pitch of the wire meshes 29a-29d is 300 μm, 250 μm, 180 μm and 150 μm, respectively. Although 4 wire meshes are used in this embodiment, mesh sections having five or more different sizes may be provided in order to enhance the accuracy in the evaluation of the non-uniformity of sharpness. Also, various values may be used for these size, thickness and pitch of these meshes.

Figure 5:
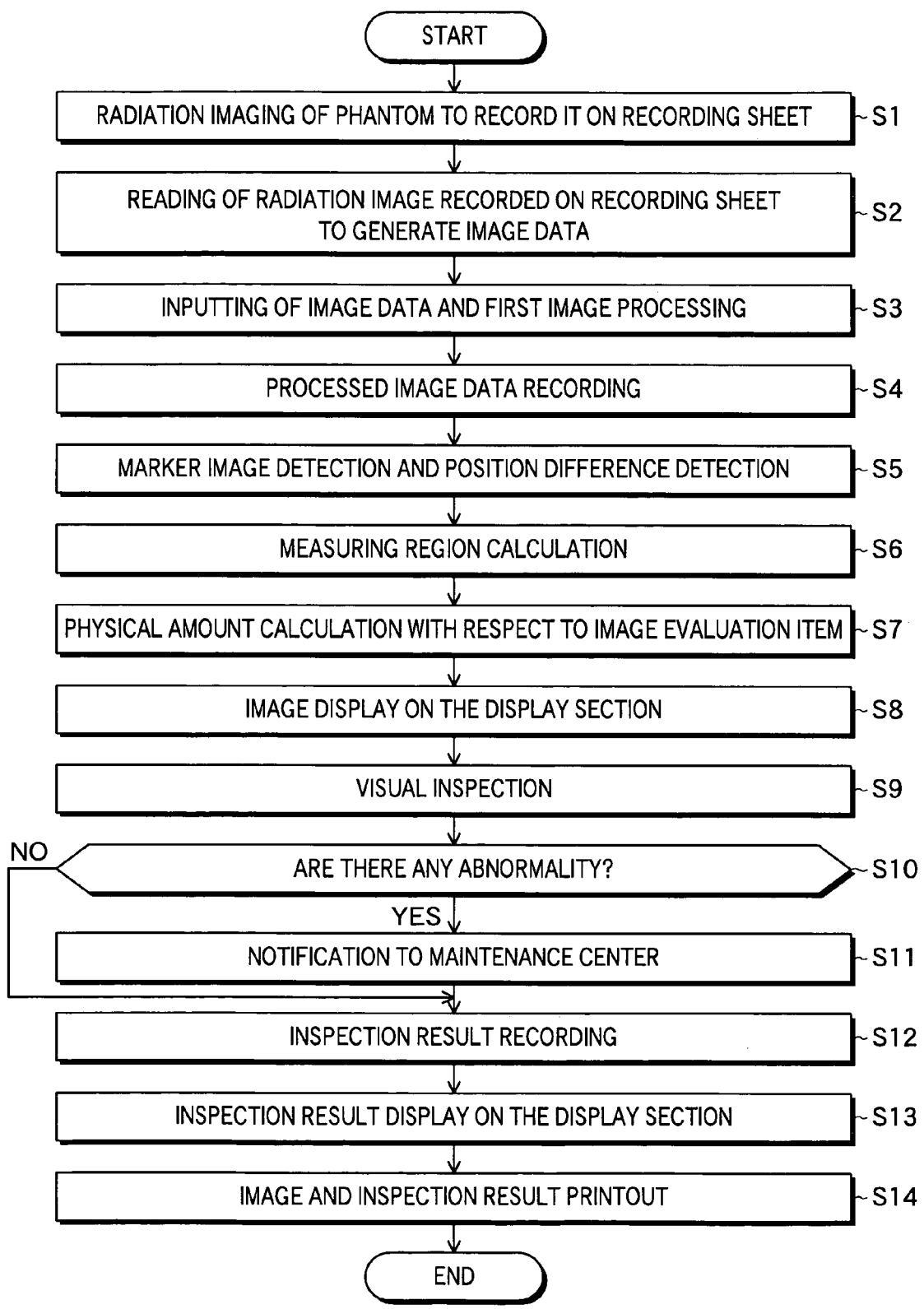
FIG. 5 is a flowchart illustrating the inspection method of the radiation imaging system according to first embodiment of the present invention.

Next, the inspection method of the radiation imaging system according to the first embodiment of the present invention will be described with reference to FIGS. 1-5. The inspection method of the radiation imaging system according to this embodiment is, in the radiation imaging system as shown in FIGS. 1 and 2, carried out by using the QC phantom 20 as shown in FIG. 3. FIG. 5 is a flowchart for illustrating the inspection method of the radiation imaging system according to this embodiment.

First of all, at step S1, the radiation imaging apparatus 100 performs radiation imaging by using the QC phantom 20 as the object, and records the radiation image information on the recording sheet 10. Then, at step S2, the medical image reading apparatus 200 reads the radiation image information recorded in the recording sheet 10 to generate image data. At step S3, in the image processing section 401, the medical image processing apparatus 300 performs a first image processing including standardization, gradation processing, logic read processing and so on with respect the image data which is inputted from the medical image reading apparatus 200. At step S4, the image data, which has subjected to the first image processing, is recorded in the image data recording section 411 of the hard disk 410. Further, when information incident to the image is inputted accompanied with the image data, the information incident to the image is also recorded in the hard disk 410.

At steps S5-S7, the CPU 400 reads out a predetermined program from the QC program recording section 414, and carries out the same.

First, at step S5, the marker position detecting section 402 detects the positions of the marker images representing three markers 24a-24c based on the image data which has been subjected to the image processing. Then, the comparison calculating section 403 compares the positions of the plurality of detected marker images and the reference positions of the marker images in the phantom image which are previously recorded in the parameter file 412. Thus, an amount of position difference from the reference position of the phantom image in the radiation image is calculated.

Here, when the radiation imaging is carried out, there may be a case where the QC phantom 20 is disposed being misaligned with respect to an appropriate position. In the case where the radiation imaging is carried out under such situation, a position difference of a phantom image is generated with respect to the reference positions on the recording sheet in the parallel direction and the rotational direction within a predetermined range. Or, there may be a case, when the radiation imaging is carried out, the QC phantom 20 is placed with upside down or being reversed. In such cases, it is possible to recognize the disposition of the QC phantom 20 at the time imaging by detecting the positions of three marker images. As for the method of detecting the positions of the marker images and the method of calculating the amount of position difference in the parallel direction and the rotational direction will be described in detail later.

At step S6, the measuring region calculating section 404 calculates positions of the images of image quality measuring patterns (pattern images), which are used for quantitative evaluation, on the recording sheet 10 (hereinafter, a region including the positions is referred to as measuring region). In this embodiment, in the patterns used for the quantitative evaluation, there are included the copper step patterns 25, the edge detecting patterns 26, and copper scale patterns 28 as shown in FIG. 3. The information about the positions of these patterns in the case where no position difference is generated (hereinafter, a region including the positions is referred to as reference region), i.e., the coordinates of the start point and the end point of pixels corresponding to the reference region are previously recorded in the parameter file recording section 412. The measuring region calculating section 404 calculates the measuring region in the actually obtained radiation image based on the position difference of the phantom image, which is calculated at step S5, and the above-mentioned information about the reference region. The method of calculating the measuring region will be described later.

At step S7, the measuring section 405 recognizes the pattern images corresponding to the image quality evaluation items based on the measuring region, which has been calculated at step S6, and measures physical amount, which is necessary for evaluating the linearity of brightness, scanning accuracy, sharpness, contraction ratio and so on of the image, on the basis of the corresponding image data which has been subjected to the image processing.

Besides, at step S8, the display section 320 displays the radiation image of the QC phantom 20 based on the image data, which has been subjected to the image processing. At step S9, the operator visually performs inspection as to the image quality evaluation items such as low contrast resolution and sharpness based on the radiation image displayed on the display section 320, and inputs the inspection results to the medical image processing apparatus 300 by using the input section 310 as shown in FIG. 2. For example, the low contrast resolution is inspected by measuring the number of the members, which are visually recognized by the operator, from among the plurality of members included in the Burgere's phantom 27 for each diameter. Also, the visual sharpness is inspected by measuring the number of the wire meshes which are visually recognized by the operator. The operator may perform visually inspection by using the radiation image of the QC phantom 20 which is outputted from the printer 330.

At step S10, the determination section 406 determines whether or not any abnormality is found in the inspection results. This determination is made in such manner that, for example, basic values are previously set on the basis of one inspection result or an average of plural inspection results in the inspection result record information, which is recorded in the inspection result recording section 411, and it is determined whether or not the present inspection result is within a allowable range between a maximum value and a minimum value or the like, which are calculated based on the basic values.

As a result of this determination, when some abnormality is found in the inspection results, the processing proceeds to step S11, and the CPU 400 notifies the abnormality to the maintenance center 530. The notification to the maintenance center 530 may be made through a central control section of the RIS 500 or the HIS 510.

On the other hand, as a result of the determination at step S10, when no abnormality is found, the processing proceeds to step S12, and the inspection results and the determination result are recorded in the inspection result recording section 411 of the hard disk 410. Also, at step S13, these inspection results and the determination result are outputted to the display section 320 and displayed on the display. Further, at step S14, these inspection results and the determination result are also outputted to the printer 330, and if required, printed out along with the radiation image of the QC phantom 20.

Next, the method of detecting the position of the marker images in the radiation image, which is made at step S5 in FIG. 5, with reference to FIGS. 6A-10.

Figure 6A:
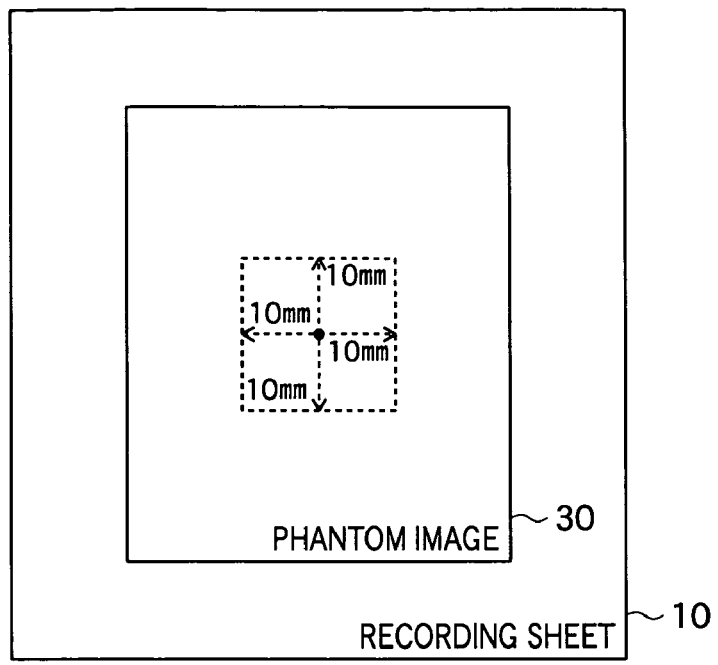
FIGS. 6A and 6B are diagrams illustrating the range where the position of the phantom image is out of alignment with respect to a recording sheet.
Figure 6B:
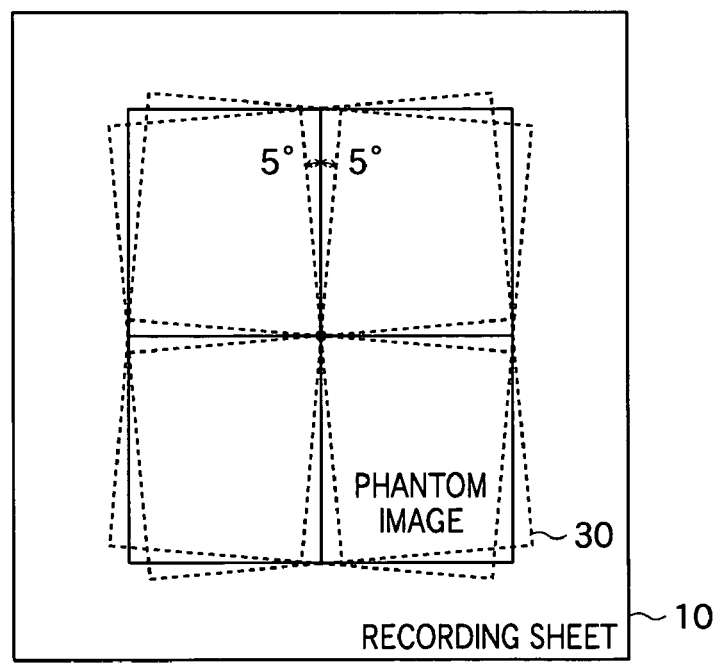

First, before detecting the position of the marker images, the range to be searched for markers is determined. FIGS. 6A and 6B show the positional relationship between a recording sheet and a recorded phantom image. Also, FIGS. 7A and 7B are diagrams for illustrating the range to be searched for markers.

As the basis for determining the marker search area, as shown in FIG. 6A, the position difference in parallel of the phantom image 30 with respect to the recording sheet 10 is within a range of ±10 mm in up/down and right/left wherein a position where the center of the recording sheet 10 coincides with the center of the phantom image 30 is determined as the reference. Further, as shown in FIG. 6B, the amount of position difference in the rotational direction of the phantom image 30 with respect to recording sheet 10 (the difference of an angle) is within a range of +5° wherein a state where the longitudinal side of the recording sheet 10 and the longitudinal side of the phantom image 30 are parallel to each other is determined as the reference angle.

Figure 7A:
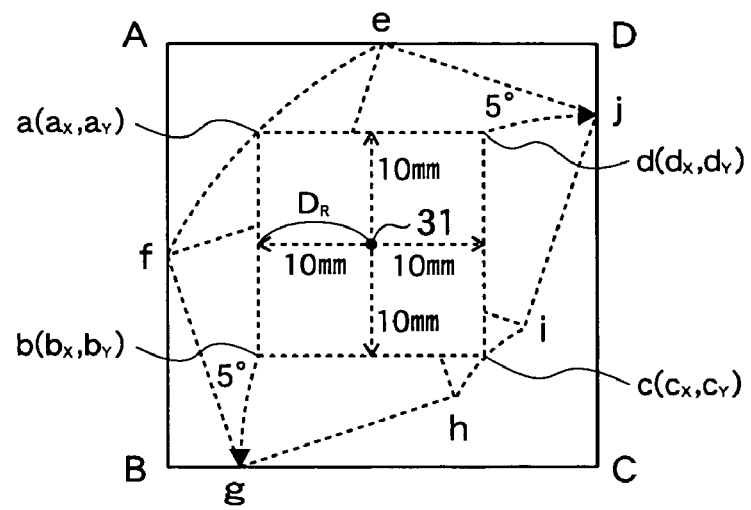
FIGS. 7A and 7B are diagrams illustrating the range where the marker image exists.

As a consequence, as shown in FIG. 7A, the range where a marker image 31 at left upper of the phantom image 30 can exist is within a region "abcd" by making parallel shift, and within a region "efghij" by making rotational shift. Accordingly, when detecting the marker image 31, it is preferred to search for the marker image 31 while limiting the marker search area to the inside of the region "efghij". In order to simplify the processing, however, the region "ABCD", which is a circumscribed quadrangle of the region "efghij", is determined as the marker search area. In FIG. 7A, although the marker image 31 is represented by a dot, it is necessary to take the size of the marker image 31 into consideration when searching the marker image 31.

Figure 7B:
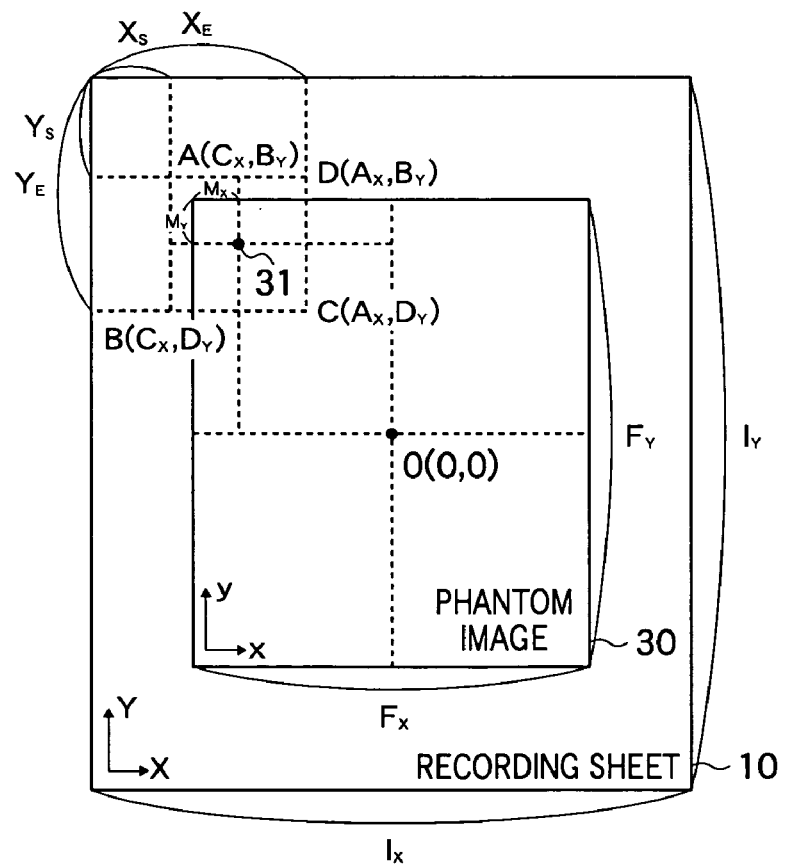

As shown in FIG. 7B, the coordinate of each point and the size of each section are defined as described below. In FIG. 7B, the phantom image 30 in the state where the position difference with respect to the recording sheet 10 is not generated is shown. The X-axis and the Y-axis are respectively parallel to the two sides of the recording sheet 10, which are perpendicular to each other, and the x-axis and the y-axis are respectively parallel to the two sides of the phantom image 30 which are perpendicular to each other. Hereinafter, when the central point "O" of the recording sheet 10 is determined as the zero point, it is defined, if not otherwise defined, that the rightward direction in FIG. 7B indicates the positive direction of X and the upward direction indicates positive direction of Y.

$I_X$ . . . traversal size of the recording sheet 10

$I_Y$ . . . longitudinal size of the recording sheet 10

$F_X$ . . . traversal size of the phantom image 30

$F_Y$ . . . longitudinal size of the phantom image 30

$M_X$ . . . x-direction distance from the upper left of the phantom image 30 to the center of the marker image 31

$M_Y$ ... y-direction distance from the upper left of the phantom image 30 to the center of the marker image 31

$D_R$ ... maximum parallel shift distance of the marker image 31 on the X-axis and the Y-axis with respect to the marker image position as the reference in the case of no position difference of the phantom image 30

$(X_S, Y_S)$ ... coordinate of the point "A" with respect to the upper left of the recording sheet 10 as the zero point $(X_E, Y_E)$ ... coordinate of the point "C" with respect to the upper left of the recording sheet 10 as the zero point Here, when the upper left of the recording sheet 10 is determined as the zero point, the rightward direction in FIG. 7B is the positive direction of X, and the downward direction thereof is the positive direction of Y.

a $(a_X, a_Y)$ ... coordinate of point "a" when the central point "O" of the recording sheet 10 is determined as the zero point b $(b_X, b_Y)$ ... coordinate of point "b" when the central point "O" of the recording sheet 10 is determined as the zero point c $(c_X, c_Y)$ ... coordinate of point "c" when the central point "O" of the recording sheet 10 is determined as the zero point d $(d_X, d_Y)$ ... coordinate of point "d" when the central point "O" of the recording sheet 10 is determined as the zero point A $(C_X, B_Y)$ ... coordinate of point "A" when the central point "O" of the recording sheet 10 is determined as the zero point C $(A_X, D_Y)$ ... coordinate of point "C" when the central point "O" of the recording sheet 10 is determined as the zero point Further, the radius of the marker image 31 is defined as $M_R$. Further, the maximum rotation angle of the phantom image 30 in the positive direction is defined as $\alpha$, the maximum rotation angle thereof in the negative direction is defined as $\beta$, and the maximum parallel shift distance is defined as $D_R$, while taking as the reference the case where the longitudinal sides of the recording sheet 10 and the longitudinal sides of the phantom image 30 are parallel to each other. The maximum rotation angle is defined in the direction where the angle increases (counterclockwise). In the case as shown in FIGS. 6A and 6B, $\alpha=0.5°$, $\beta=0.5°$ and $D_R=10$ mm.

By using the values defined above, the search region "ABCD" of the marker image as shown in FIG. 7A is determined by a rectangle which has a line passing two points of $(X_S, Y_S)$ and $(X_E, Y_E)$ expressed by the following expressions (1) and (2) as the diagonal line where the zero point is at the upper left of the recording sheet 10. As shown in FIG. 7B, the two sides of the rectangle perpendicular to each other are parallel to the X-axis and the Y-axis, respectively.

$$(X_S, Y_S) = (I_X/2 + C_X, I_Y/2 - B_Y) \quad (1)$$

$$(X_E, Y_E) = (I_X/2 + A_X, I_Y/2 - D_Y) \quad (2)$$

Here, $C_X$, $D_Y$, $A_X$ and $B_Y$ are expressed by the following expressions (3)-(6).

$$C_X = a_X \cos(-\alpha) + a_Y \sin(-\alpha) \quad (3)$$

$$D_Y = -b_X \sin(-\alpha) + b_Y \cos(-\alpha) \quad (4)$$

$$A_X = d_X \cos(-\beta) + d_Y \sin(-\beta) \quad (5)$$

$$B_Y = -a_X \sin(-\beta) + a_Y \cos(-\beta) \quad (6)$$

Further, $(a_X, a_Y)$, $(b_X, b_Y)$ and $(d_X, d_Y)$ are expressed by the following expressions (7)-(9):

$$(a_X, a_Y) = (-F_X/2 + M_X - D_R - M_R, F_Y/2 - M_Y + D_R + M_R) \quad (7)$$

$$(b_X, b_Y) = (-F_X/2 + M_X - D_R - M_R, F_Y/2 - M_Y - D_R - M_R) \quad (8)$$

$$(d_X, d_Y) = (-F_X/2 + M_X + D_R + M_R, F_Y/2 - M_Y + D_R + M_R) \quad (9)$$

Figure 8:
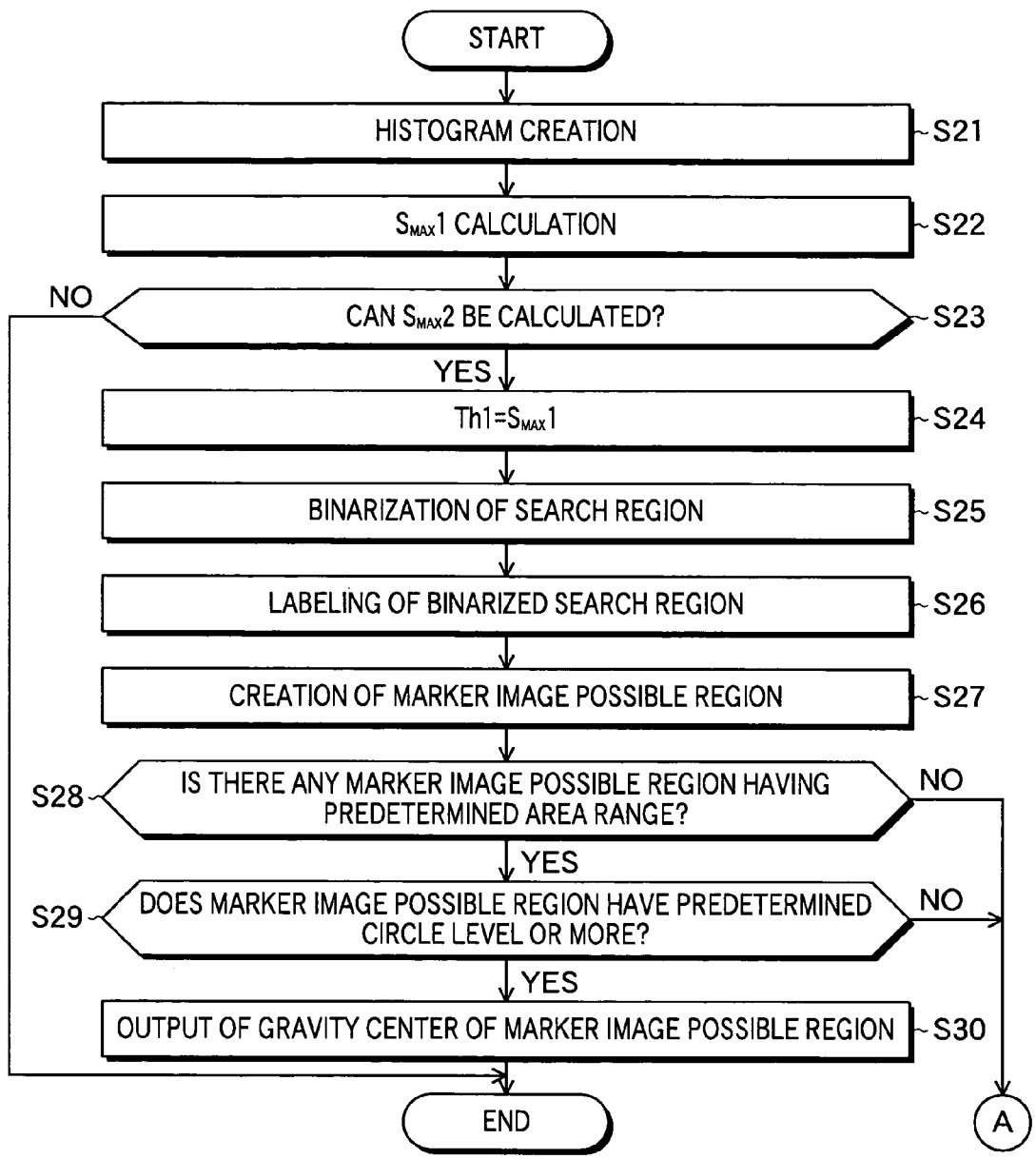
Figure 9:
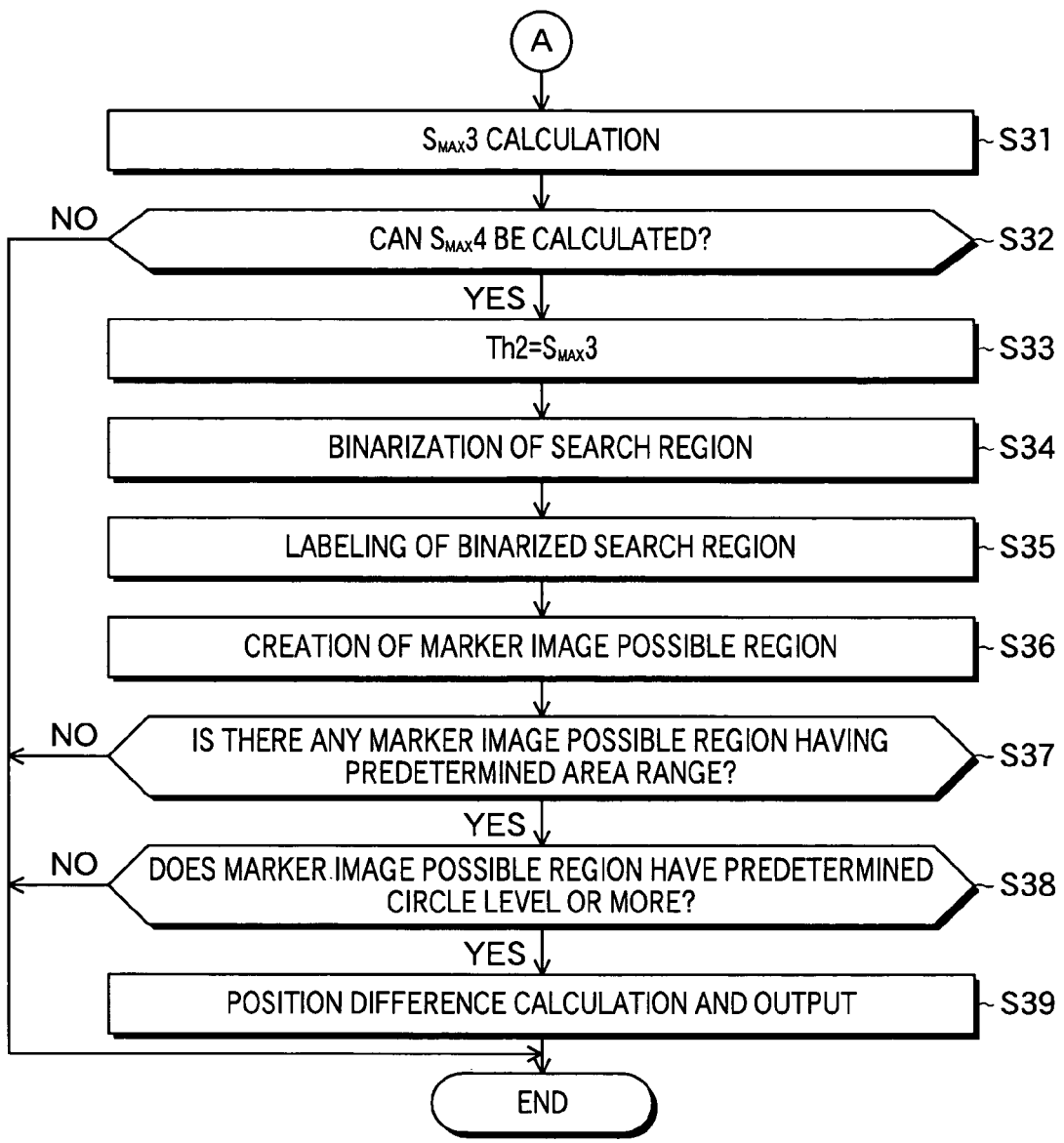

FIGS. 8 and 9 are flowcharts showing the operation of the medical image processing apparatus 300 (FIG. 2) for detecting the marker image and calculating the position difference of the phantom image by using the same.

In this embodiment, by utilizing the brightness and shape of the marker image 31, the marker image 31 is detected. The reason of this is as follows. In the radiation image, which is obtained by imaging the QC phantom 20, there are included not only the marker image but also external background of the QC phantom 20, images inside the QC phantom including various patterns and the base, the edge of the QC phantom, the aperture and so on, and therefore, there is a possibility that such images are included in the marker search region defined by the above expressions (1) and (2).

First, at steps S21 to S24 in FIG. 8, the marker position detecting section 402 in the medical image processing apparatus 300 detects the brightness of the image within the search region, and thereby determines the possibility of the existence of the marker image 31 within the search region.

That is, at step S21, a histogram, which indicates density distribution (frequency of appearance of specific brightness) of the images within the search region, is created. FIG. 10 is a histogram showing the density distribution of images within the search region. The QL-value allotted to the traversal axis indicates an amount that becomes larger as the brightness of image becomes lower (closer to black), and the frequency allotted to the longitudinal axis indicates an amount corresponding to the number of pixels having the QL-value.

Then, at step S22, the histogram is scanned from the maximum QL-value toward the minimum QL-value. The reason of this is that., when some external background image out of the QC phantom is included in the search region, the marker image 31 becomes a region having a high density next to the background image, while when no background image is included therein, the marker image 31 becomes the region having the highest density. After the frequency value has exceeded a maximum value of the QL-value, which is generated by the marker image 31 and a background image out of the QC phantom, a QL-value when the frequency value becomes lower than the threshold value Thd for the first time is obtained and the value is determined as $S_{max}1$. Here, the threshold value Thd is a value that depends on the spatial resolution and the bit resolution.

At step S23, the histogram is continuously scanned from $S_{MAX}1$ toward the minimum QL-value and it is determined whether or not the frequency value exceeds the threshold value Thd again. When the frequency value exceeds the threshold value Thd again, the QL-value at that point is determined as $S_{MAX}2$, and the processing proceeds to step S24. In this case, it is determined that there is a possibility that the marker image 31 exists with in the search region, and at step S24, $S_{Max}1$ is set up as the threshold value Th1 in terms of the QL-value. On the other hand, when the value of the frequency does not exceed the threshold value Thd again, i.e., when $S_{MAX}2$ can not be obtained, since the inside of the search region is a uniform image, it is determined that the marker image 31 does not exist within the search region and the detection of marker image is terminated.

FIG. 10 shows a histogram in the case where the densities of the background image and the marker image 31 are close to each other. In this case, the heaps of the frequency of the background image and the marker image 31 are connected to each other continuously. However, in the case where the densities of the background image and the marker image 31 are not close to each other, the heaps of the frequency of the background image and the marker image 31 are separated from each other. Accordingly, in the case where the densities of the background image and the marker image 31 are not close to each other, the threshold value Th1, which has been set up at step S24, becomes the threshold value of the background image which is the maximum density region, while in the case where the densities of the background image and the marker image 31 is close to each other, the threshold value Th1 becomes the threshold value of the background image and the marker image.

Then, at steps S25-S29, the marker position detecting section 402 determines the shape of the regions of which QL-value exceeds the threshold value Th1. That is, at step S25, the search region is classified into two regions, i.e., a region where the QL-value is not less than the threshold value Th1 and a region where the QL-value is less than the threshold value Th1. Then, at step S26, pixels included in the region where the QL-value is not less than the threshold value Th1 are labeled. Further, at step S27, the regions where the labeled pixels in contact with each other are collected into one region, and this region is determined as a marker image possible or candidate region.

Then, at step S28, it is determined whether or not any marker image possible region having an area within a predetermined range is included. This determination is made based on whether or not the following expression (10) is satisfied.

$$0.5\pi M_R^2 < (\text{area of the marker image possible region}) << 1.5\pi M_R^2 \quad (10)$$

As a result of the determination based on the expression (10), when any marker image possible region, which has area within the predetermined range, is included, the processing proceeds to step S29. On the other hand, when any marker image possible region, which has area within the predetermined range, is not included, it is determined that the marker image 31 does not exist in the region where the QL-value exceeds the threshold value Th1, and the processing proceeds to step S31 as shown in FIG. 9.

At step S29, it is determined whether or not the circle level or roundness of the marker image possible region is a predetermined value or more. The determination method is as described below. First, it is assumed that a circle, which has the same area as the marker image possible region, exists at the gravity point of the marker image possible region. Assuming that the area of the marker image possible region is S, the radius R of the assumed circle is represented by $R=(S/\pi)^{1/2}$.

Then, assuming that an area of a region common to the marker image possible region and the region of the assumed circle is U, and the circle level or roundness of the marker image possible region is expressed as U/S. And it is determined whether or not the circle level or roundness U/S satisfies the following expression (11):

$$U/S \geq 0.8 \quad (11)$$

As a result of the determination based on the expression (11), when the circle level or roundness of the marker image possible region is not less than a predetermined value, the processing proceeds to step S30. On the other hand, when the circle level or roundness of the marker image possible region is less than the predetermined value, it is determined that the marker image 31 does not exist in the region where the QL-value is not less than the threshold value Th1, and the processing proceeds to step S31 as shown in FIG. 9.

At step S30, by using the coordinate of the gravity point of the marker image possible region while taking the upper left of the recording sheet 10 as the zero point, the comparison calculating section 403 of the medical image processing apparatus calculates the position difference of the phantom image with respect to the parallel direction and the rotational direction, and outputs the results thereof to the measuring section 405.

On the other hand, as a result of determination at step S28 or S29 in FIG. 8, when it is determined that the marker image 31 does not exist in the region where the QL-value is not less than the threshold value Th1, it is determined whether or not the marker image 31 exists in the region where the QL-value is less than the threshold value Th1 as shown in FIG. 9.

First, at steps S31-S33, the marker position detecting section 402 determines the possibility of existence of the marker image 31 within the search region. That is, at step S31, in the histogram shown in FIG. 10, a scan pertaining to the QL-value is made from the threshold value Th1 to the minimum QL-value. In the case where a QL-value when the QL-value is less than the threshold value Thd is obtained, the value is determined as $S_{MAX}3$. Then, at step S32, the scan is continuously carried out from $S_{MAX}3$ toward the minimum QL-value, and it is determined whether the frequency value exceeds the threshold value Thd again. When the frequency value exceeds the threshold value Thd again, the QL-value at that point is determined as S4, and the processing proceeds to step S33. In this case, it is determined that there is a possibility the marker image 31 exists in search region, and $S_{MAX}3$ is set up as the threshold value Th2 in terms of the QL-value (step S33). On the other hand, when the frequency value does not exceed the threshold value Thd again, i.e., when $S_{MAX}4$ can not be obtained, since the image excluding the background image within search region is uniform, it is determined that the marker image 31 does not exist in the search region, and the scanning for the marker image is terminated.

Then, at step S34-S38, the marker position detecting section 402 determines the shape of the region where the QL-value is not less than the threshold value Th2 and is less than Th1. That is, at step S34, the search region is classified into two regions, i.e., a region, where the QL-value is not less than the threshold value Th2 and is less than Th1, and the other region other than the above. Then, at step S35, the pixels included in the region, where the QL-value is not less than the threshold value Th2 and is less than Th1, are labeled. Further, at step S36, regions where the labeled pixels are in contact with each other are collected into one region and this region is determined as the marker image possible region.

Then, at step S37, the marker position detecting section 402 determines, as same as the processing at step S28, whether or not the marker image possible region, which has an area within a predetermined range, is included. When the marker image possible region, which has an area within a predetermined range, is included, the processing proceeds to step S38. On the other hand, when the marker image possible region, which has an area within a predetermined range, is not included, it is determined that the marker image 31 does not exist within the search region, and the marker detection processing is terminated.

At step S38, as same as the processing at step S29, it is determined whether or not the circle level or roundness of the marker image possible region is a predetermined value or more. As a result, when the circle level or roundness of the marker image possible region is not less than the predetermined value, the processing proceeds to step S39. On the other hand, when the circle level or roundness of the marker image possible region is less than the predetermined value, it is determined that the marker image 31 is not included within the search region, and the marker detection processing is terminated. Further, at step S39, as same as the processing at step 630, in the comparison calculating section 403, the position difference of the phantom image is calculated, and the calculated amount of position difference is outputted to the measuring section 405.

The marker position detecting section 402 also performs the marker detection processing as described above in terms of the marker images at the upper right and the lower right of the phantom image 30. Alternatively, the marker position detecting section 402 may performs the marker detection processing with respect to the four corners of the phantom image 30 to detect the tree marker images, thereby determine whether not the QC phantom 20 has imaged being reversed or upside down. In such case, the medical image processing apparatus 300 may perform image processing on the image data so that the obtained radiation image is inversed upside down, right/left or 180° turn.

Next, the method of calculating the measuring region as the measuring object when the quantitative evaluation is carried out, which is made at step S6 in FIG. 5, will be described. In this embodiment, the measuring region is calculated using a radiation image of two markers 24a and 24b, which are indicated at the upper portion in FIG. 3.

Figure 11A:
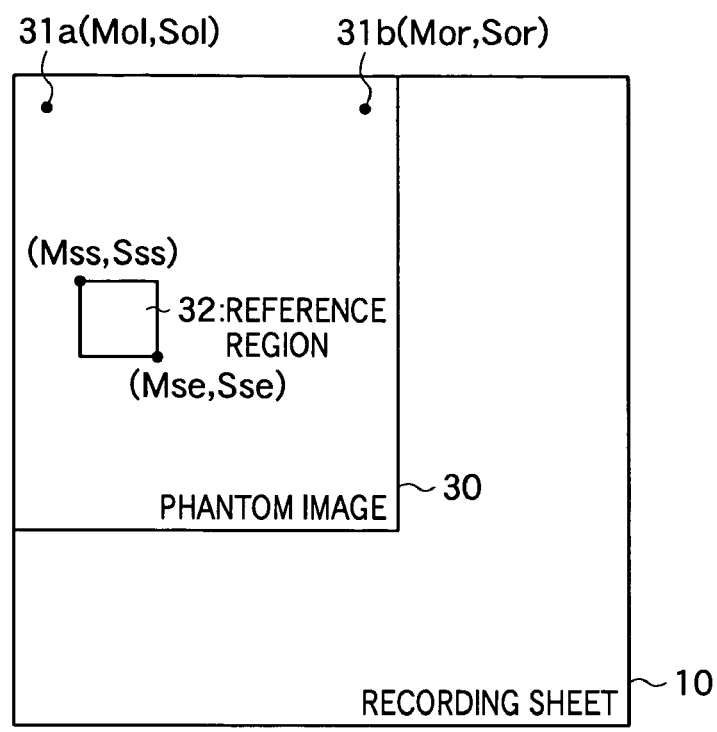
FIGS. 11A and 11B are diagrams illustrating a phantom image recorded in the recording sheet.
Figure 11B:
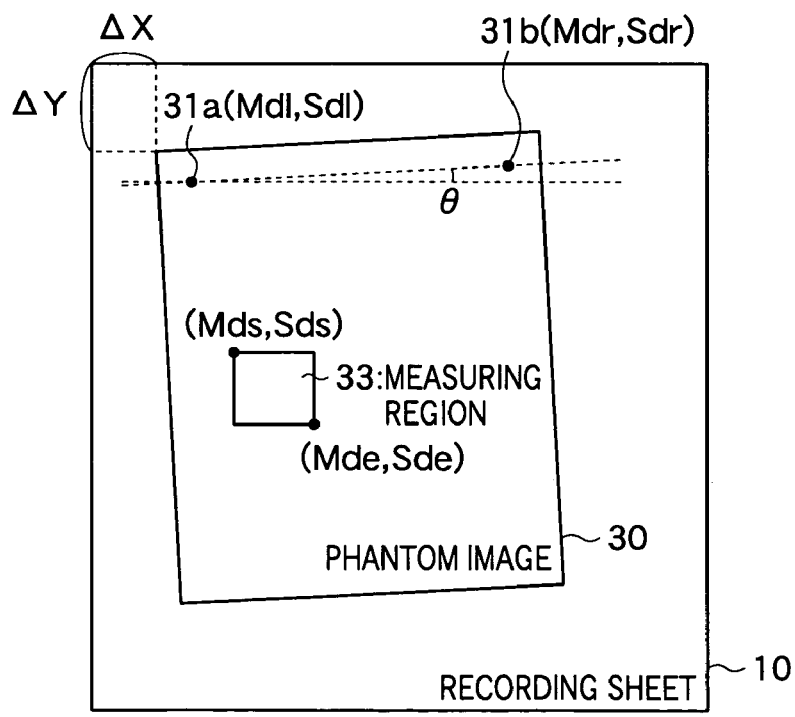

FIGS. 11A and 11B show a phantom image 30 recorded in the recording sheet 10 respectively. FIG. 1A shows the case where the phantom image 30 is properly recorded at the reference position of the recording sheet 10. That is, in FIG. 11A, the positions of the upper left of the recording sheet and the upper left of the phantom image are coincide with each other, and the longitudinal side of the recording sheet and the longitudinal side of the phantom image are parallel to each other. FIG. 11B shows, compared to the case in FIG. 1A, a case where the phantom image is out of alignment. In FIGS. 11A and 11B, to simplify the description, only the marker image 31a at the upper left of the phantom image 30, the marker image 31b at the upper right thereof, a reference region 32, and a measuring region 33 are indicated.

In FIG. 1A, assuming that the upper left of the recording sheet 10 as the zero point, the coordinate of the marker image 31a is defined as (Mol, Sol), the coordinate of the marker image 31b is defined as (Mor, Sor), the coordinate of the start point of the reference region 32 is defined as (Mss, Sss), and the coordinate of the end point is defined as (Mse, Sse). Further, in FIG. 11B, the coordinate of the marker image 31a is defined as (Mdl, Sdl), the coordinate of the marker image 31b is defined as (Mdr, Sdr), coordinate of the start point of the measuring region 33 is defined as (Mds, Sds), and the coordinate of the end point thereof id defined as (Mde, Sde).

Using these values, the inclination angle θ of the phantom image 30 and the offset value (ΔX, ΔY) are expressed by the following expressions (12)-(14).

$$\theta = \arctan\{(Sdl - Sdr)/(Mdl - Mdr)\} \quad (12)$$

$$\Delta X = Mdl - Mol \quad (13)$$

$$\Delta Y = Sdl - Sol \quad (14)$$

Accordingly, by using the coordinate values of the reference region 32, which are previously recorded in the parameter file, the coordinate of the measuring region 33 is obtained by the following expressions (15) and (16).

$$\begin{pmatrix} Mds \\ Sds \end{pmatrix} = \begin{pmatrix} \cos\theta & -\sin\theta \\ \sin\theta & \cos\theta \end{pmatrix} \begin{pmatrix} Mss - Mol \\ Sss - Sol \end{pmatrix} + \begin{pmatrix} \Delta X \\ \Delta Y \end{pmatrix} \quad (15)$$

$$\begin{pmatrix} Mde \\ Sde \end{pmatrix} = \begin{pmatrix} \cos\theta & -\sin\theta \\ \sin\theta & \cos\theta \end{pmatrix} \begin{pmatrix} Mse - Mol \\ Sse - Sol \end{pmatrix} + \begin{pmatrix} \Delta X \\ \Delta Y \end{pmatrix} \quad (16)$$

That is, when carrying out the inspection, using the above two points as the diagonal points, a rectangle of which two sides perpendicular to each other are parallel respectively to each side of the recording sheet 10 is obtained as the measuring object.

As described above, according to the first embodiment of the present invention, by using a QC phantom, which includes a material for attenuating or shielding the radiation and a plurality of members disposed on the base plate for enabling the measurement of at least the linearity, the sharpness and the contraction ratio with respect to the image read out by the image reading apparatus, the inspection of the image reading apparatus is carried out based on the image data which is generated by reading out the radiation image. Accordingly, it is made possible to inspect up to the detailed items by one imaging.

Also, according to this embodiment, it is made possible to easily and reliably detect the position of the phantom image by using at least two markers disposed in the QC phantom. By building an inspection system of radiation imaging system by using a QC phantom as described above, it is made possible to automate the inspection operation while ensuring the correctness and reliability, while preventing the inspection operation from being interrupted or becoming complicated, and the reliability of the inspection can be ensured.

In this embodiment, when detecting the position of the marker image, the search region is previously set up and scanning is carried out within the search region. Owing to this arrangement, compared to the case where the entire region of the radiation image is scanned, it is possible to reduce the processing time. Alternatively, in the same time, the accuracy of the detection can be increased. The search region may set up in accordance with, for example, a setting method in which only the upper quarter portion of the radiation image is scanned.

Figure 12:
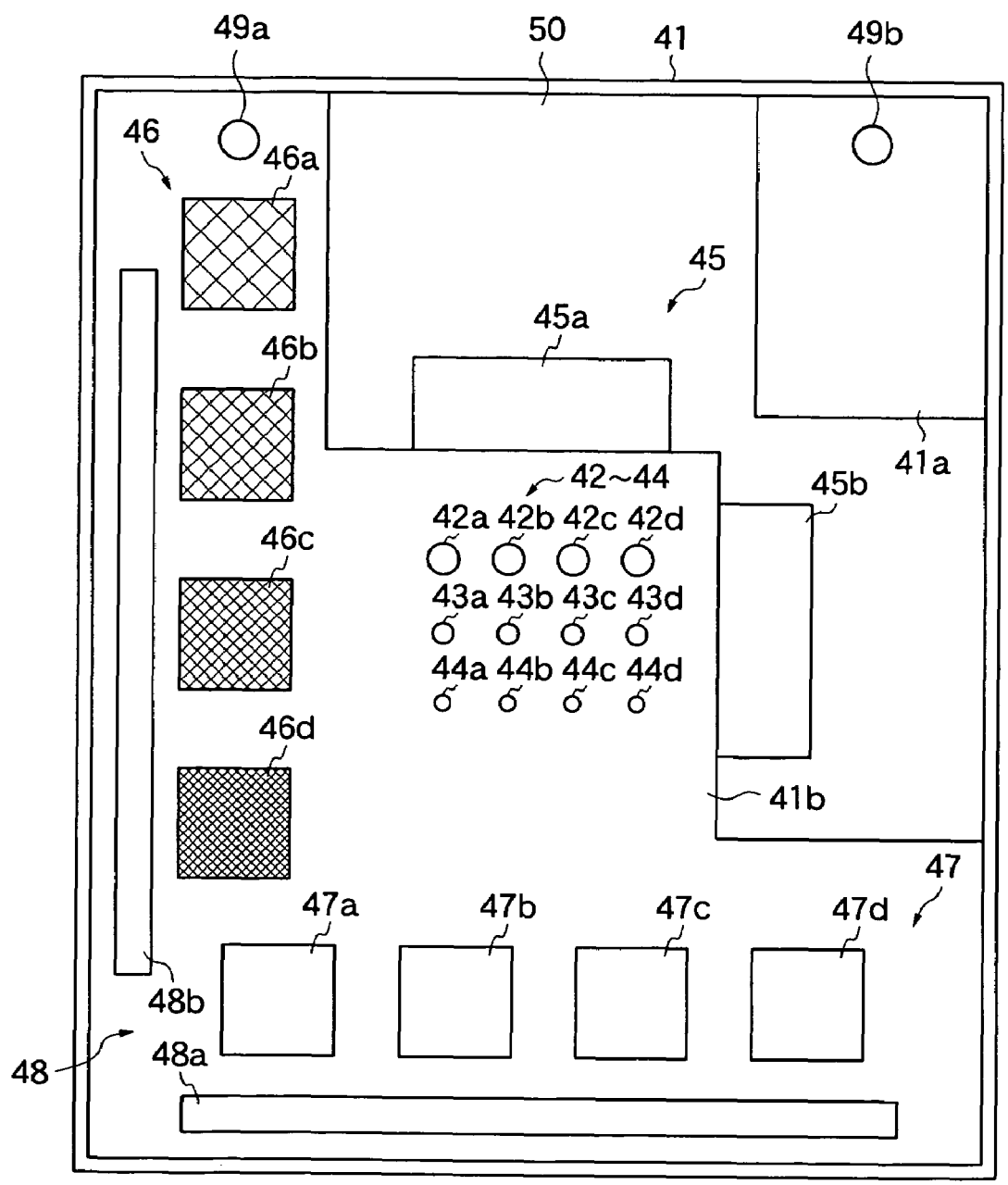
FIG. 12 is a plan view showing an example of modification a phantom according to one embodiment of the present invention.

FIG. 12 shows an example of modification of the QC phantom according to the above-mentioned embodiment of the present invention. The QC phantom 40 includes a base plate 41 and a plurality of image quality measuring patterns 42-49, which are constituted of a plurality of members disposed on the base plate 41. The base plate 41 is formed of, for example, a rectangular copper plate, which provides a mechanical stability to the QC phantom 40 and provides an X-ray beam quality appropriate for image analysis. Also in this embodiment, as same as the QC phantom 20 as shown in FIG. 3, the base plate 41 may be placed in an acrylic case.

As shown in FIG. 12, disposed in the QC phantom 40 as the image quality evaluating patterns, are Burgere's phantoms (contrast resolution patterns) 42-44 for visual evaluation of low contrast resolution of an image, edge detecting patterns 45 for quantitative evaluation of sharpness of the image, wire mesh patterns 46 for visual evaluation of sharpness of the image, step patterns 47 for visual evaluation and quantitative evaluation of linearity and dynamic range of the image, and scale patterns 48 for quantitative evaluation of contraction ratio of the image. Further, in the QC phantom 40, markers 49a and 49b for detecting the position of these patterns are disposed in regions excluding empty regions 41a and 41b. The empty regions 41a and 41b may be used for quantitative evaluation of S/N ratio of a radiation image signal.

Figure 13:
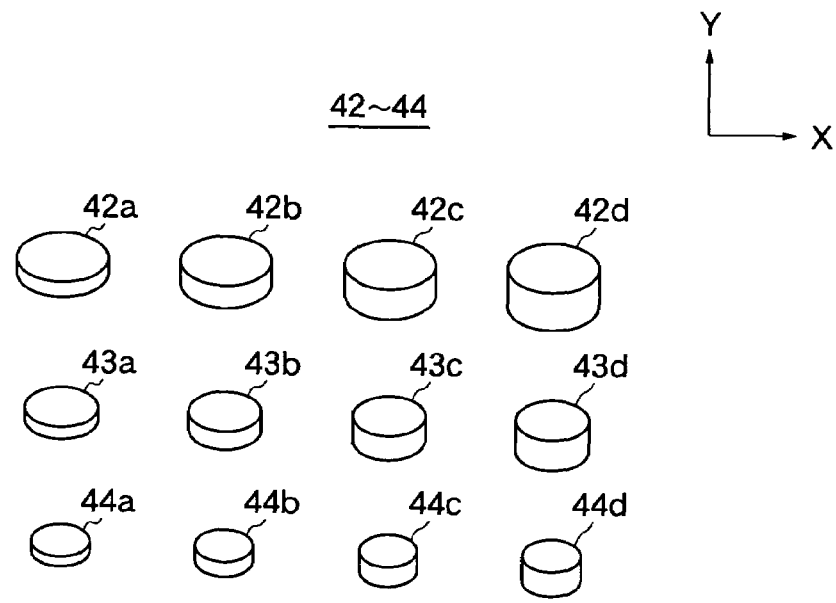
FIG. 13 is a perspective view showing a Burgere's phantom (contrast resolution patterns) included in the phantom as shown in FIG. 12.

FIG. 13 is a perspective view showing Burgere's phantoms 42-44. The Burgere's phantoms 42-44 include, for example, 12 steps 42a-42d, 43a-43d and 44a-44d formed of acrylic resin. These steps 42a-42d, 43a-43d and 44a-44d are disposed in a matrix-like configuration such that the thickness thereof is different from each other in the X-direction and the size (diameter) thereof is different from each other in the Y-direction. As the members used for Burgere's phantoms, in addition to a resin material such as acrylic, a metal material may be used.

The edge detecting patterns 45 are patterns used as the reference for geometrical measurement, and include sharp-angled edge portions 45a and 45b respectively for measuring MTF (modulation transfer function) in the X-direction and Y-direction. Each of the sharp-sharp-angled edge portions 45a and 45b is formed of a tungsten plate, and at the outside thereof, a lead plate 50 is disposed. By virtue of this arrangement, in the peripheral region of the sharp-angled edge portions 45a and 45b, since a large part of the irradiated radiation is shield, any influence from the surrounding can be prevented, and therefore, the sharpness can be evaluated further precisely. Here, the above-mentioned MTF is obtained by differentiating the radiation image of the edge detecting pattern 45a or 45b to obtain a line spread function, and then subjecting it to a Fourier transformation.

In addition to the above, in place of the edge detecting patterns 45, the image quality-evaluating pattern for quantitative evaluation of the sharpness of image including at least one of an edge-detecting pattern, a slit pattern and a rectangular wave pattern may be used. Owing to this arrangement, both of the quantitative evaluation and the visual evaluation in terms of the sharpness can be carried out.

Figure 14:
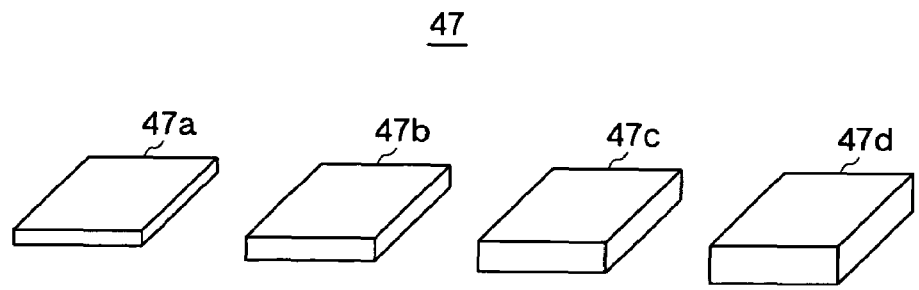
FIG. 14 is a perspective view showing step patterns included in the phantom as shown in FIG. 12.

FIG. 14 is a perspective view showing step patterns 47. The step patterns 47 include four rectangular copper plates 47a-47d having thicknesses different from each other. As described above, different from the step patterns 25 as shown in FIG. 3, every member included in the step patterns may be formed of a copper plate.

In this example of modification, as the image quality evaluating patterns for visually evaluating the sharpness of image, the wire mesh patterns 46 are used. However, in addition to the above, patterns including at least one of wire mesh pattern, bar pattern and radial pattern may be used.

Further, in this example of modification, the disposition of the wire mesh pattern 46 and the step patterns 47 is different from the disposition in the QC phantom 20 as shown in FIG. 3. Thus, the disposition of the image quality measuring patterns in the QC phantom may be variously changed.

In this example of modification, two markers 49a and 49b are disposed on the base plate 41. In the case where there is no possibility that the QC phantom 40 is mounted in reverse or upside down at radiation imaging, at least only two markers 49a and 49b will do for detecting the position of the phantom image.

In the above-described QC phantom according to one embodiment of the present invention and the example of modification thereof, the markers are formed by cutting through the copper plate. To the contrary, the markers may be formed, for example, by using lead having a thickness larger than predetermined value so that the radiation, which has transmitted the markers, has an energy level lower than predetermined value under any imaging conditions. In this case, the marker position detecting section 402 as shown in FIG. 2 detects only in the region where the radiation dose is lower than a prescribed value. As a consequence, the markers can be stably detected with a simple algorithm. The above-prescribed value may be determined or changed by using the results obtained by monitoring the dose of the radiation.

Further, as for the shape of the markers, as far as the coordinates of at least two points in the radiation image can be identified, any shape such as a dot-like shape, a line-like shape, plane-like shape is available. Furthermore, in the case where the amount of position difference of the phantom image is expected to be large, it may be arrange to form an appropriate allowable range on a monitor screen on which the phantom image is display ed. Thereby, when the phantom image is displayed exceeding the allowable range, a message to the operator is displayed to instruct to image the QC phantom 20 again.

Figure 15:
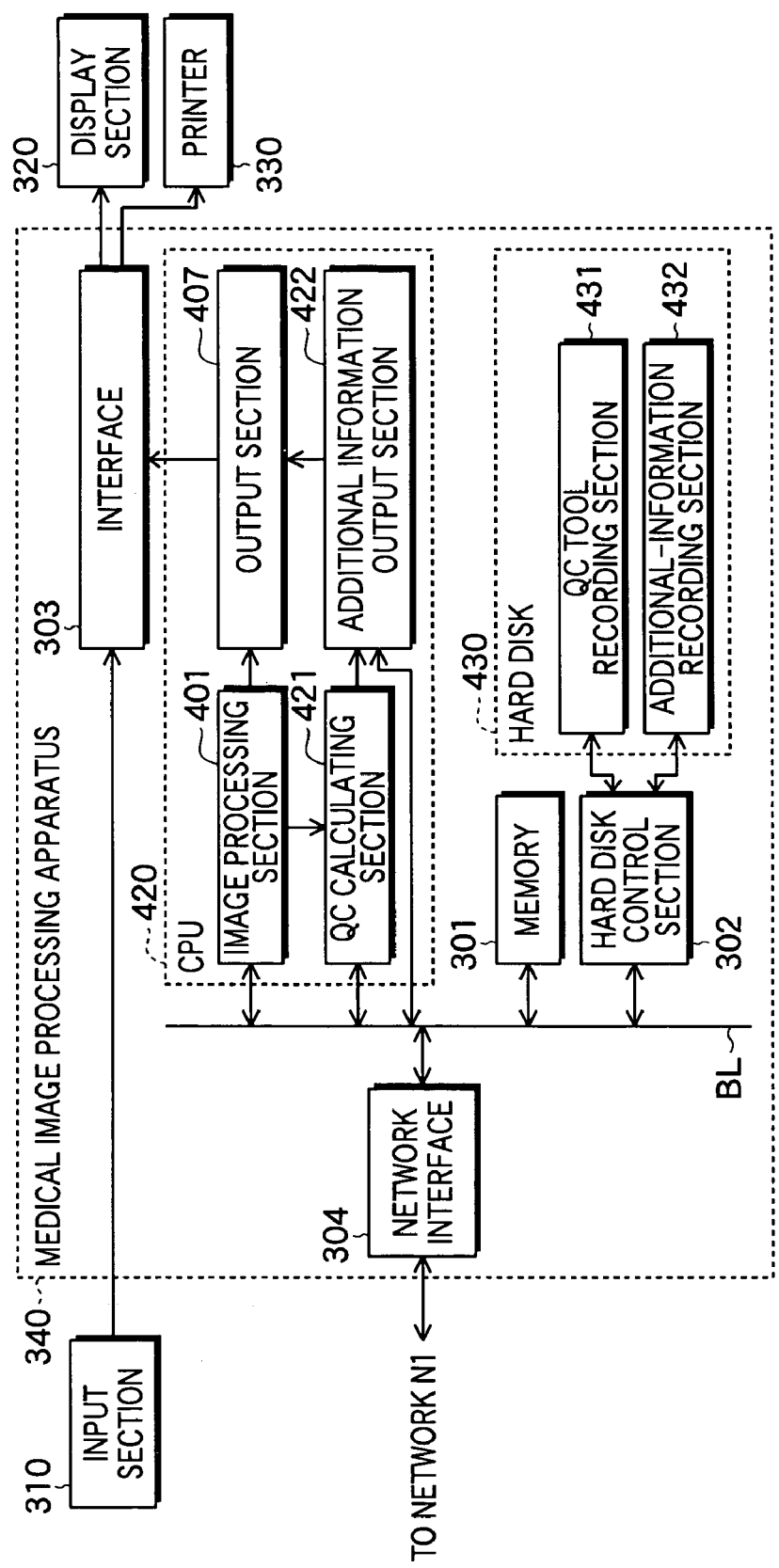
FIG. 15 is a block diagram showing a part of a radiation imaging system including medical image processing apparatus according to a second embodiment of the present invention.

Next, a medical image processing apparatus according to a second embodiment of the present invention will be described. FIG. 15 is a block diagram showing a part of a radiation imaging system including medical image processing apparatus according to this embodiment.

In place of the medical image processing apparatus 300 as shown in FIG. 1, the radiation imaging system as shown in FIG. 15 has a medical image processing apparatus 340. In place of the CPU 400 and the hard disk 410 as shown in FIG. 2, the medical image processing apparatus 340 shown in FIG. 15 has a CPU 420 and a hard disk 430. The configuration other than the above is the same as the radiation imaging system and the medical image processing apparatus as shown in FIG. 1 and FIG. 2.

The CPU 420 includes a QC calculating section 42.1 that performs the calculation for quantitatively evaluating in terms of the obtained radiation image and an additional information output section 422 that outputs additional information in terms of the image. In this embodiment, although the QC calculating section 421 is incorporated in the CPU 420, but the configuration is not limited thereto. For example, the QC calculating section may be incorporated in a host computer, which controls the entire system, or a personal computer, in which only the QC calculating section is incorporated, may be used.

Recorded in the hard disk 430 are a basic program for operating the CPU 440, a program (QC tool) for performing the inspection of the radiation imaging system, information and so on to be used for such processing. In FIG. 15, a tool recording section 431 and an additional-information recording section 432 are shown. The CPU 440 reads out the above information to store it in the memory 301 so as to be used for various processing.

Recorded in the QC tool recording section 431 is a program (software) for quantitative evaluation corresponding to a plurality of image quality evaluating patterns of the QC phantom 20. The software for quantitative evaluation has various signal processing algorithms. These algorithms include every logic means necessary for calculating physical amount representing the quality of the radiation imaging system when receiving the image data representing the radiation image of the image quality evaluating patterns of the QC phantom 20.

Recorded in the additional information recording section 432 are imaging conditions at the radiation imaging such as X-ray tube voltage in the radiation imaging apparatus 100 and distance between the radiation source and the object, image reading conditions in the medical image reading apparatus 200, image processing conditions in the image processing section 401, and image display conditions such as a number of pixels, a number of gradation steps and necessity of image processing in the display section 320, and so on. This additional information is read out from the hard disk as appropriate, used in the QC calculating section 421 and outputted through the additional information output section 422.

Next, the operation of the medical image processing apparatus 340 as shown in FIG. 15 will be described.

In this embodiment, as shown in FIG. 3 or FIG. 12, inspection of the radiation imaging system is carried out by using the QC phantom formed with image quality measuring patterns for visual evaluation and quantitative evaluation for one image quality measurement item.

When the image data representing radiation image of QC phantom 10 as shown in FIG. 3 is inputted from the medical image reading apparatus 200 (FIG. 1) to medical image processing apparatus 340 through the network N1, the image processing section 401 performs a predetermined image processing such as gradation processing on the input image data.

Then, the CPU 420 reads out the programs for the quantitative evaluation from the QC tool recording section 431 and carries out the programs in order. That is, the QC calculating section 421 performs quantitative evaluation with respect to the image data representing the radiation image of the QC phantom 20, which has been processed in the image processing section 401, as to various image quality evaluation items corresponding to the image quality evaluating patterns. At that time, the QC calculating section 421 reads out the additional information from the additional information recording section 432 and uses the additional information when carrying out the QC calculation.

The output section 407 outputs the data representing the results of the quantitative evaluation, which is obtained in the QC calculating section 421, to the display section 320 or the printer 330. At this time, the additional information output section 422 may output the additional information such as the image display conditions, image processing conditions, image reading conditions and the imaging conditions at radiation imaging, which are recorded in the additional information recording section 432. Thereby, the above information may be displayed or printed out on the display screen or film along with the pattern image and the quantitative evaluation results. Owing to this, the evaluation conditions of the image can be easily and reliably confirmed resulting in a further precise verification.

On the other hand, the medical image processing apparatus 340 outputs the image data of the pattern image corresponding to the predetermined image quality evaluation items on which the visual evaluation is made to allow the display section 320 or the printer 330 to display or print out the same. An operator carries out the visual evaluation in terms of the display ed pattern image. Thus, the quantitative evaluation and the visual evaluation are made with respect to the radiation image of various image quality evaluating patterns included in the QC phantom 20, thereby the performance and the constancy of the radiation imaging system are verified.

Here, the medical image processing apparatus 340 outputs the data as to the image quality evaluation items on which both the visual evaluation and the quantitative evaluation are made, so that pattern image for the visual evaluation and the results of the quantitative evaluation are display ed or printed out on the display or the film. As a consequence to this, the operator can carry out the visual evaluation as to the image quality evaluation items on which both the visual evaluation and the quantitative evaluation are made, while readily taking into consideration the results of the quantitative evaluation which are displayed or printed out on the display or the film. Accordingly, the correctness of the evaluation is increased.

The displaying on the display section 320 or printing out to a film of the pattern image, results of the quantitative evaluation and the additional information may be carried out based on the operation by the operator, or may be automatically carried out based on the control by the CPU 420. Also in this embodiment, as same as the first embodiment of the present invention, it may be arranged so that, when any abnormality is found in the inspection results, the fact is notified to the maintenance center 530 as shown in FIG. 1.

As described above, according to the second embodiment of the present invention, the visual evaluation and the objective and quantitative evaluation as to various image quality parameters such as contrast resolution, S/N ratio, sharpness, linearity, dynamic range and contraction ratio can-be made by using one QC phantom. Accordingly, the verification of the performance and constancy of the radiation imaging system can be readily carried out resulting in a reduction of manpower, time and cost. Since the visual evaluation and the quantitative evaluation as to at least one image quality evaluation item can be made by using one QC phantom, both measurement results can be readily compared, and the results of the quantitative evaluation can be utilized in the visual evaluation. Accordingly, a further objective evaluation can be made, thus the correctness of the constancy evaluation can be increased. Further, by displaying the evaluation results of the quantitative evaluation along with the radiation image of the image quality-evaluating patterns, the visual evaluation, to which the quantitativeness of the quantitative evaluation is added, can be readily made. Accordingly, the correctness of the evaluation is further increased. Furthermore, by displaying the additional information such as image display conditions, image processing conditions, imaging conditions and results of the quantitative evaluation along with the radiation image of the image quality evaluating patterns, evaluating conditions and so on of the image can be readily confirmed. Accordingly, a further correct evaluation can be made.

This embodiment may includes the case where one image quality evaluating pattern corresponding to one image quality evaluation item is used for both of the visual evaluation and the quantitative evaluation, the case where an image quality evaluating pattern for visual evaluation and image quality evaluating pattern for the quantitative evaluation corresponding to one image quality evaluation item are used respectively for the visual evaluation and the quantitative evaluation and the case where the former and later image quality-evaluating patterns are simultaneously included.

Figure 16:
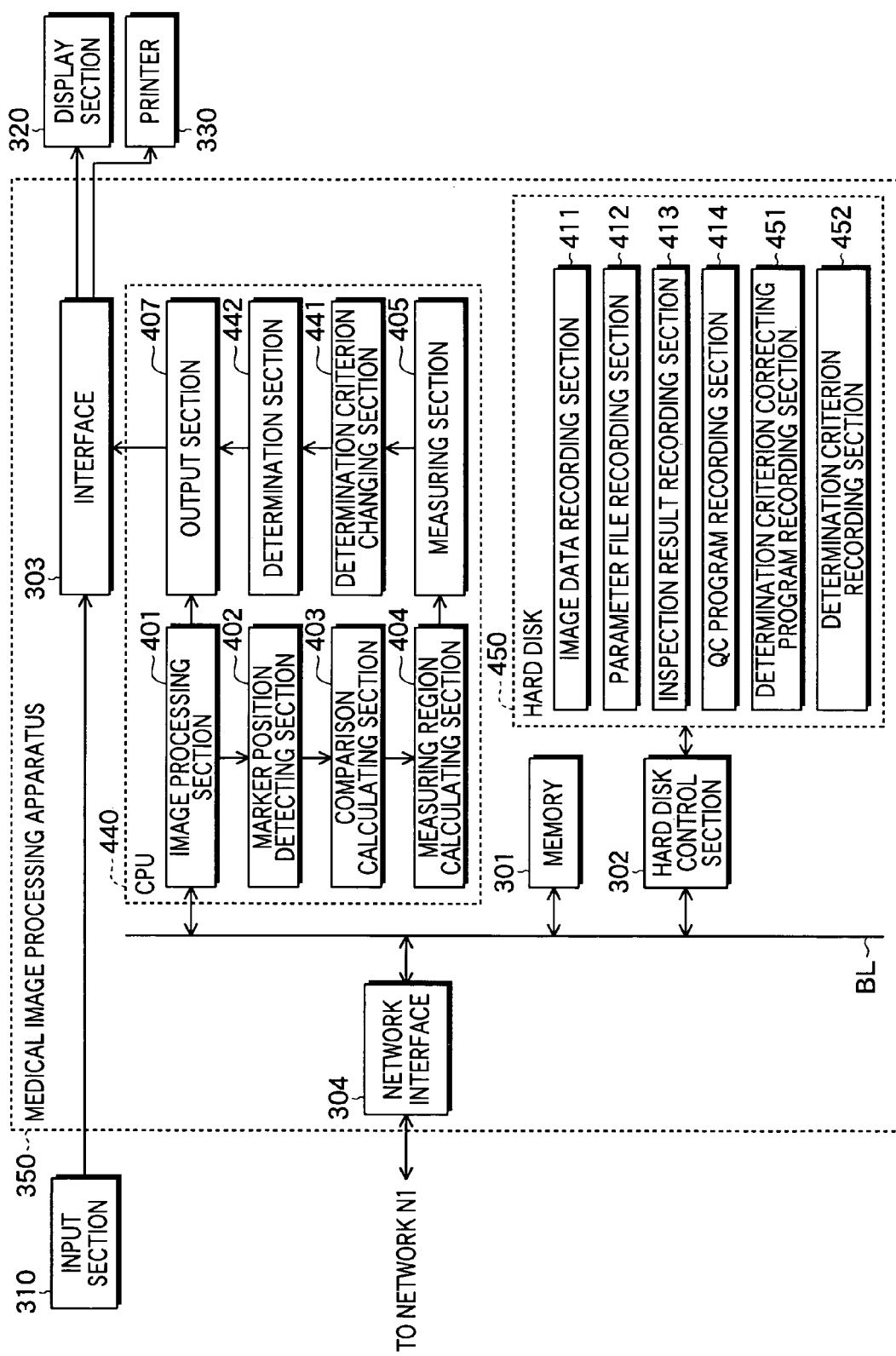
FIG. 16 is a block diagram showing a part of a radiation imaging system including medical image processing apparatus according to a third embodiment of the present invention.

Next, a medical image processing apparatus according to a third embodiment of the present invention will be described. FIG. 16 is a block diagram showing a part of a radiation imaging system including medical image processing apparatus according to this embodiment.

In place of the medical image processing apparatus 300 as shown in FIG. 1, the radiation imaging system as shown in FIG. 16 has a medical image processing apparatus 350. In place of the CPU 400 and the hard disk 410 as shown in FIG. 2, the medical image processing apparatus 350 as shown in FIG. 16 has a CPU 440 and a hard disk 450. The configuration other than the above is the same as the radiation imaging system as shown in FIG. 1 and FIG. 2.

The CPU 440 has a determination criterion changing section 441 that changes the reference for evaluating pattern image based on the amount of position difference of the phantom image, and a determination section 442 that determines whether or not abnormality exists in each image quality evaluation item based on a physical amount, which is calculated with respect to the pattern image, and the changed determination criterion and determines the image quality of the phantom image. The other functions of the CPU 440 other than the above are the same as those described referring to FIG. 2.

Recorded in the hard disk 450 are a basic program for operating the CPU 440, a program for performing the inspection of the radiation imaging system, information and so on to be used for such processing. Shown in FIG. 16 are an image data recording section 411, a parameter file recording section 412 in which information or the like as to the reference position of the phantom image is stored, an inspection result recording section 413, a QC program recording section 414, a determination criterion correcting program recording section 451 in which a program for changing a determination criterion at evaluating the image quality based on the amount of position difference of the phantom image is stored, and a determination criterion recording section 452 in which a determination criterions corresponding to the image quality evaluation items are stored. The CPU 440 reads out the above information and stores it into the memory 301 for various processing.

Figure 17:
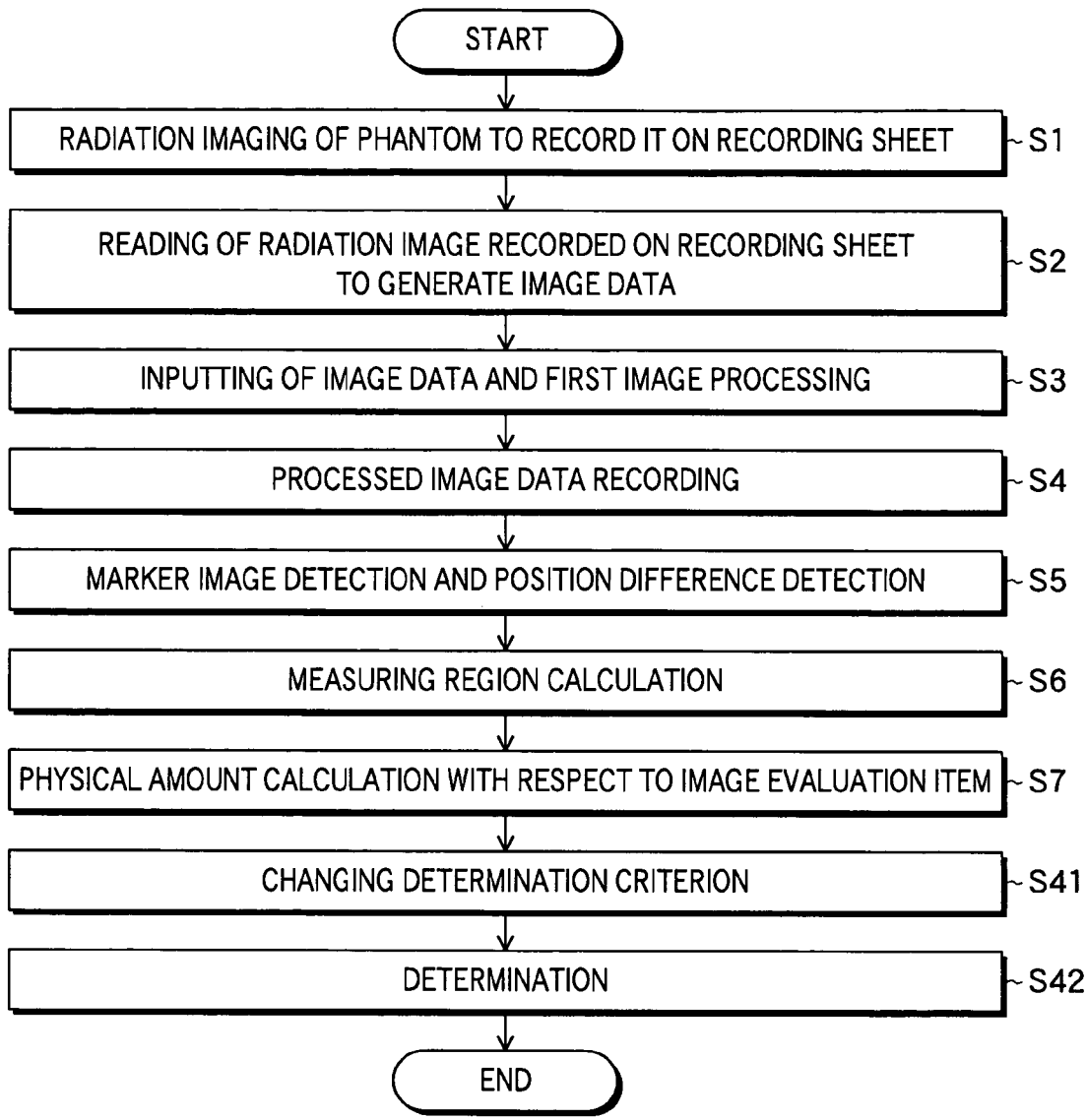
FIG. 17 is a flowchart showing the inspection method of the radiation imaging system according to the third embodiment of the present invention.

Next, the inspection method of the radiation imaging system according to the third embodiment of the present invention will be described with reference to FIGS. 16 and 17. FIG. 17 is a flowchart showing the inspection method of the radiation imaging system according to this embodiment.

First, at steps S1-S7, as same as the above-described first embodiment of the present invention referring to FIG. 5, by using the image data representing the radiation image of the QC phantom 20, which has been obtained by radiation imaging, the amount of position difference of the phantom image is calculated. An inspection as to the measuring region, which is obtained based on the above, is made and the physical amount required for the evaluation of the image quality is calculated. The generated radiation image is displayed on the display section 320.

Next, at step S41, the CPU 440 reads out the correcting program from the determination criterion-correcting program recording section 451 and carries out the correcting program. That is to say, the determination criterion changing section 441 reads out the determination criterion of the pattern image from the determination criterion recording section 452, and based on the amount of position difference of the phantom image (refer to FIGS. 11A and 11B) in the parallel direction and rotational direction, and changes the determination criterion for evaluating the pattern image. Further, at step S42, the determination section 442 evaluates the physical amount with respect to the pattern image, which has been calculated in the measuring section 405, based on the changed determination criterion. The determination result obtained as described above is outputted to the display section 320 and so on through the output section 407. Also in this embodiment, as same as step S11 in FIG. 5, it may be arranged so that, when any abnormality is found in the inspection results, the abnormality is notified to the maintenance center 530 by the CPU 440.

As described above, according to the third embodiment of the present invention, the determination criterion of the image quality evaluation items is changed corresponding to the amount of position difference of the phantom image. Accordingly, automation of the inspection operation is accelerated as well as the accuracy of the inspection can be further enhanced.

Figure 18:
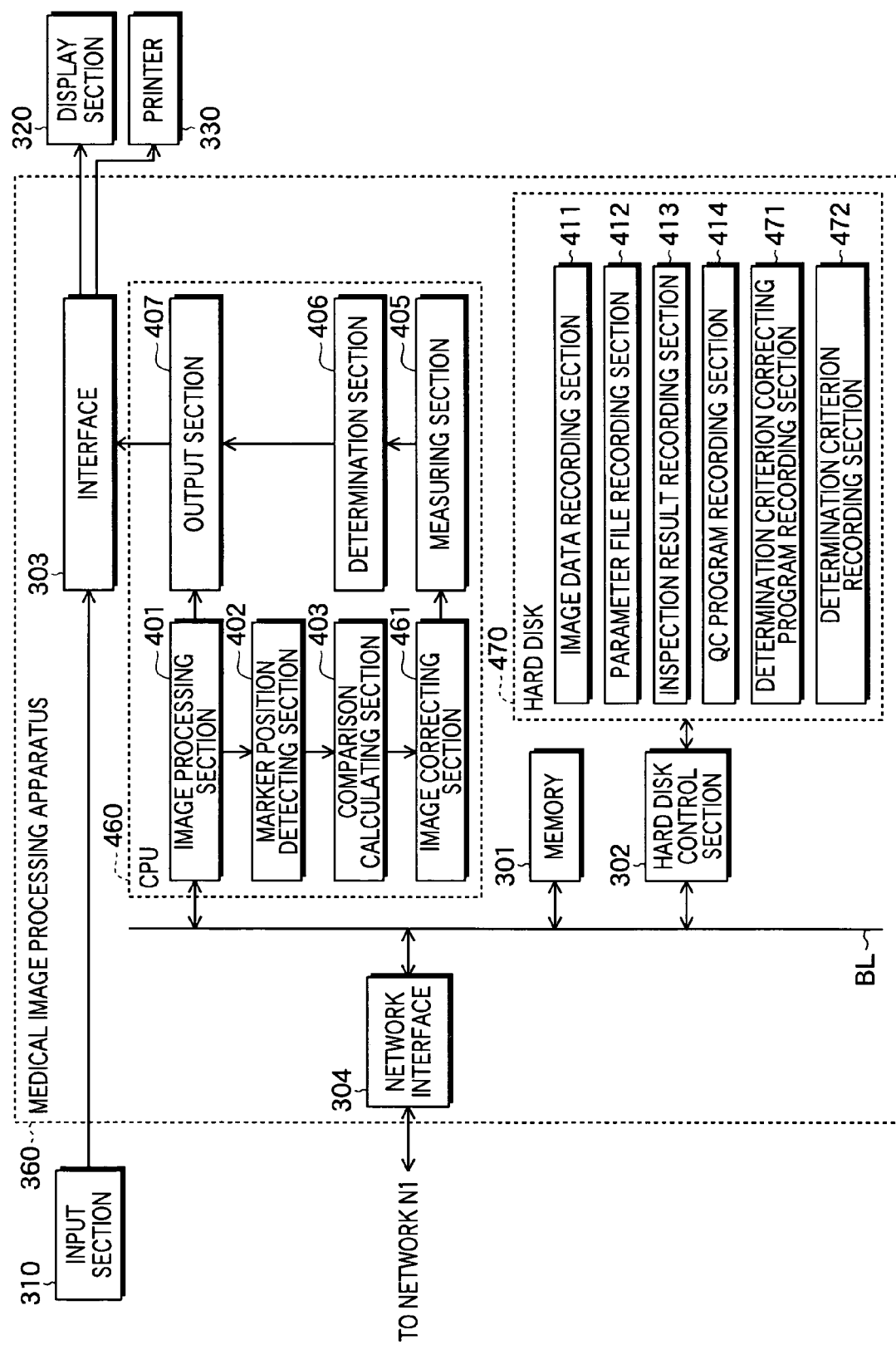
FIG. 18 is a block diagram showing a part of a radiation imaging system including medical image processing apparatus according to a fourth embodiment of the present invention.

Next, a medical image processing apparatus according to a fourth embodiment of the present invention will be described. FIG. 18 is a block diagram showing a part of a radiation imaging system including medical image processing apparatus according to this embodiment.

In place of the medical image processing apparatus 300 as shown in FIG. 1, the radiation imaging system as shown in FIG. 18 has a medical image processing apparatus 360. In place of the CPU 400 and the hard disk 410 as shown in FIG. 2, the medical image processing apparatus 360 as shown in FIG. 18 has a CPU 460 and a hard disk 470. The configuration other than the above is the same as the radiation imaging system as shown in FIG. 1 and FIG. 2.

The CPU 460 has an image correcting section 461 that corrects the generated radiation image to an ideal position based on the amount of position difference of the phantom image. The other functions of the CPU 440 other than the above are the same as those described referring to FIG. 2.

Figure 19:
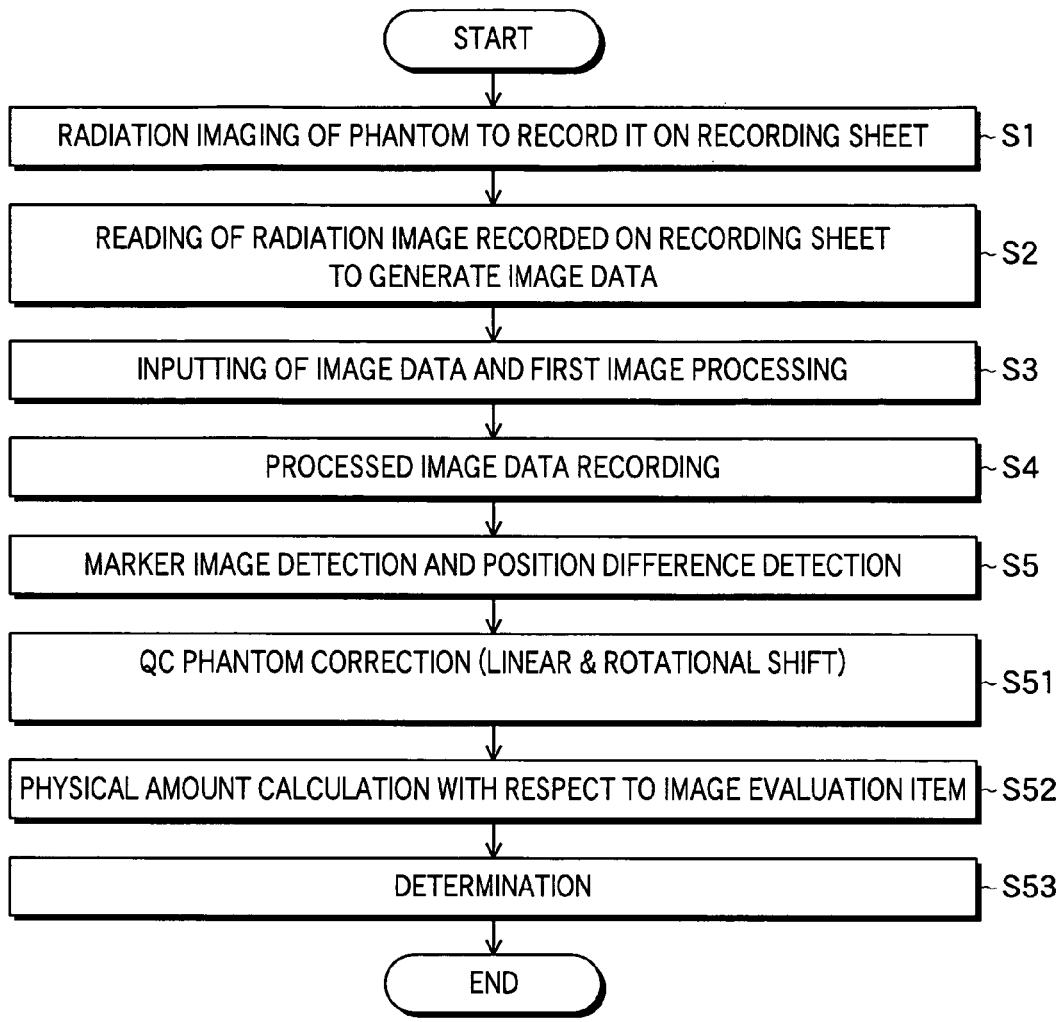
FIG. 19 is a flowchart showing the inspection method of the radiation imaging system according to the fourth embodiment.

Recorded in the hard disk 470 are a basic program for operating the CPU 460, a program for performing the inspection of the radiation imaging system, information and so on to be used for such processing. Shown in FIG. 19, are an image data recording section 411, a parameter file recording section 412 in which information and so on with respect to the reference position of the phantom image are stored, an inspection result recording section 413, a QC program recording section 414, image correcting program recording section 471 in which a correcting program for correcting the position of the phantom image to an ideal position is stored, and a determination criterion recording section 472 in which a determination criterions corresponding to the image quality evaluation items are stored. The CPU 440 reads out the above information and stores it into the memory 301 for various processing.

Next, the inspection method of the radiation imaging system according to the fourth embodiment of the present invention will be described with reference to FIGS. 18 and 19. FIG. 19 is a flowchart showing the inspection method of the radiation imaging system according to this embodiment.

First, at steps S1-S7, as same as the above-described first embodiment of the present invention referring to FIG. 5, by using the image data representing the radiation image of the QC phantom 20, which has been obtained by radiation imaging, the amount of position difference of the phantom image is calculated. The generated radiation image is displayed on the display section 320.

Then, at step S51, the CPU 460 reads out the correcting program from the image correcting program-recording section 472 to carry out the correcting program. That is to say, the image correcting section 464 carries out the image processing to make the phantom image to perform parallel shift and rotational shift in the direction opposite to the amount of position difference, based on the amount of difference of the phantom image (refer to FIGS. 11A and 11B) in the parallel direction and rotational direction which has been obtained at step S5 in FIG. 5. Thereby, the amount of position difference of the phantom image including the pattern image is corrected.

Then, at step S52, with respect to the corrected pattern image, the measuring section 405 calculates the physical amount corresponding to image quality evaluation item. Then, at step S53, the determination section 406 reads out the determination criterion as to each pattern image from the determination criterion recording section 473, and based on the determination criterion, determines the physical amount with respect to the calculated pattern image. The determination result obtained as described above is outputted to the display section 320 and so on through the output section 407. Also in this embodiment, as same as step S11 in FIG. 5, it may be arranged so that, when any abnormality is found in the inspection results, the abnormality is notified to the maintenance center 530 by the CPU 460.

As described above, according to the fourth embodiment of the present invention, automation of the inspection operation is made possible. At the same time, since the determination criterions of the measuring region and the pattern image are not changed, the inspection processing can be readily carried out.

As described above, the inspection method of the radiation imaging system, the medical image processing apparatus using the same and the QC phantom used for the inspection of the radiation imaging system according to first to fourth embodiments of the present invention have been described. However, the present invention is not limited to the above-described embodiments. Within a range where the spirit of the present invention set forth in the claims of the present invention is not exceeded, various modifications are possible in designing thereof. For example, as for the recording medium for recording the transmitted radiation of the QC phantom, in addition to the photo stimulable phosphor sheet 10, a flat panel device which converts the transmitted radiation level into an electrical signal may be used.

The invention claimed is:

1. A medical image processing apparatus for evaluating image quality of a radiation image obtained by using a radiation imaging system which performs radiation imaging to record radiation image information on a recording medium, reads out the radiation image information from the recording medium to generate image data, and performs a predetermined image processing for the image data to display or output a radiation image, thereby inspecting said radiation imaging system, said medical image processing apparatus comprising:

image processing means for performing image processing on input image data;

measuring means for performing, when image data representing a radiation image obtained by imaging a phantom having a plurality of image quality evaluating patterns as to a predetermined image quality evaluation item is inputted, measurement with respect to the input image data as to said predetermined image quality evaluation item;

inputting means to be used for inputting inspection result as to said predetermined image quality evaluation item obtained by visually observing the displayed or outputted radiation image; and determination means for determining the image quality of said radiation image on the basis of measurement result obtained by said measuring means and the inspection result inputted by using said inputting means.

2. A medical image processing apparatus according to claim 1, further comprising:

position detecting means for detecting a position of said phantom in said radiation image on the basis of the input image data.

3. A medical image processing apparatus according to claim 2, wherein said position detecting means detects the position of said phantom in said radiation image by detecting images of a plurality of markers respectively disposed at positions different from each other in said phantom.

4. A medical image processing apparatus according to claim 3, wherein said plurality of markers include at least three markers.

5. A medical image processing apparatus according to claim 1, further comprising:

control means for controlling, when image data representing a radiation image obtained by radiation imaging of a phantom having an image quality evaluating pattern to be used for visual evaluation and an image quality evaluating pattern to be used for quantitative evaluation as to a predetermined image quality evaluation item is inputted, to display determination result based on the quantitative evaluation as to said predetermined image quality evaluation item together with said radiation image.

6. A medical image processing apparatus according to claim 1, further comprising:

control means for controlling to display together with said radiation image at least one of imaging condition when said radiation image has been imaged, image reading condition when said radiation image information has been read out from said recording medium, image processing condition when the input image data has been subjected to the image processing by said image processing means and display condition when said radiation image is displayed.

7. A medical image processing apparatus according to claim 1, further comprising:

recoding means for recording the measurement result obtained by said measuring means and the inspection result inputted by using said inputting means.

8. A medical image processing apparatus according to claim 1, further comprising: control means for controlling, when said determination means has determined that abnormality of the image quality exists in said radiation image, to notify a maintenance center of existence of the abnormality of the image quality.

9. A medical image processing apparatus according to claim 1, further comprising:

position detecting means for detecting, when image data representing a radiation image obtained by imaging a phantom having an image quality evaluating pattern as to at least one image quality evaluation item and a plurality of markers respectively disposed at a plurality of positions different from each other by using said radiation imaging system is inputted, a position of said phantom in said radiation image by using said plurality of markers;

comparison and calculating means for comparing the position of said phantom detected by said position detecting means with a reference position of said phantom in said radiation image to calculate an amount of difference in a linear direction and a rotational direction;

search area changing means for changing a search area, which is a region within said radiation image to be measured as to a predetermined image quality evaluation item, on the basis of the amount of difference in the linear direction and the rotational direction calculated by said comparison and calculating means;

physical amount calculating means for performing measurement as to said predetermined image quality evaluation item within the search area changed by said search area changing means, and calculating a physical amount representing characteristic of said radiation image;

determination criterion changing means for changing a determination criterion to be used for determining the image quality of said radiation image, on the basis of the amount of difference in the linear direction and the rotational direction calculated by said comparison and calculating means; and said determination means is also for determining the image quality of said radiation image by using said physical amount calculated by said physical amount calculating means, on the basis of the determination criterion changed by said determination criterion changing means.

10. A medical image processing apparatus according to claim 1, further comprising:

position detecting means for detecting, when image data representing a radiation image obtained by imaging a phantom having an image quality evaluating pattern as to at least one image quality evaluation item and a plurality of markers respectively disposed at a plurality of positions different from each other by using said radiation imaging system is inputted, a position of said phantom in said radiation image by using said plurality of markers;

comparison and calculating means for comparing the position of said phantom detected by said position detecting means with a reference position of said phantom in said radiation image to calculate an amount of difference in a linear direction and a rotational direction;

image correcting means for correcting the position of said phantom in said radiation image so that the amount of difference in the linear direction and the rotational direction calculated by said comparison and calculating means is reduced;

physical amount calculating means for performing measurement with respect to an image of said phantom, of which position is corrected by said image correcting means, as to a predetermined image quality evaluation item, and calculating a physical amount representing characteristic of said radiation image; and said determination means is also for determining the image quality of said radiation image on the basis of the physical amount calculated by said physical amount calculating means.

* * * * *